United States Patent [19]
Steinbüchel et al.

[11] Patent Number: 6,022,729
[45] Date of Patent: Feb. 8, 2000

[54] GRANULE-ASSOCIATED PROTEINS AND METHODS FOR THEIR USE IN POLYHYDROXYALKANOATE BIOSYNTHESIS

[75] Inventors: Alexander Steinbüchel, Altenberge; Ursula Pieper-Furst, Göttingen, both of Germany

[73] Assignee: Monsanto Company, St. Louis, Mo.

[21] Appl. No.: 08/702,870

[22] Filed: Aug. 26, 1996

Related U.S. Application Data

[63] Continuation of application No. 08/598,175, Feb. 7, 1996, abandoned, which is a continuation of application No. 08/500,735, Jul. 11, 1995, abandoned.

[30] Foreign Application Priority Data

Jul. 18, 1994 [GB] United Kingdom ............... 9414506

[51] Int. Cl.$^7$ ..................... C12N 1/21; C12N 15/31; C12N 15/70; C12N 15/74
[52] U.S. Cl. ................... 435/252.3; 435/252.33; 435/320.1; 435/471; 435/488; 536/23.7
[58] Field of Search ................... 536/23.2, 23.7, 536/24.1; 435/320.1, 172.3, 419, 253.3, 252.33; 47/58; 800/205

[56] References Cited

U.S. PATENT DOCUMENTS 5,502,273  3/1996  Bright et al. ........................ 800/205

FOREIGN PATENT DOCUMENTS

WO 92/19747  11/1992  WIPO.

OTHER PUBLICATIONS

Anderson, A.J. and Dawes, F.A., "Occurrence, metabolism, metabolic role, and industrial uses of bacterial polyhydroxyalkanoates," *Microbiol. Rev.* 54:450–472 (1990).

Brandl, H. et al., "*Pseudomonas oleovorans* as a source of poly(β-hydroxyalkanoates) for potential applications as biodegradable polyesters," *Appl. Environ. Microbiol.* 54:1977–1982 (1994).

Briese, B.H. et al., "*Pseudomonas lemoignei* has five poly(hydroxyalkanoic acid) (PHA) depolymerase genes: a comparative study of bacterial and eukaryotic PHA depolymerases," *J. Environ. Polym. Degrad.* 2:75–87 (1994).

Griebel, R. et al., "Metabolism of poly–β–hydroxybutyrate. I. Purification, composition, and properties of native poly–β–hydroxybutyrate granules from *Bacillus megaterium*," *Biochemistry* 7:3676–3681 (1968).

Haywood, G.W. et al., "The role of NADH– and NADPH–linked acetoacetyl–CoA reductases in the poly–3–hydroxybutyrate synthesizing organism *Alcaligenes eutrophus*," *FEMS Microbiol. Lett.* 52:259–264 (1988).

Haywood, G.W. et al., "Accumulation of a poly(hydroxyalkanoate) copolymer containing primarily 3–hydroxyvalerate from simple carbohydrate substrates by Rhodococcus sp. NCIMB 40126," *Int. J. Biol. Macromol.* 13:83–88 (1991).

Jendrossek, D. et al., "Degradation of poly(3–hydroxybutyrate), PHB, by bacteria and purification of a novel PHB depolymerase from Comumonus sp.," *J. Environ. Polym. Degrad.* 1:53–63 (1993).

Jendrossek, D. et al., "Three different proteins exhibiting NAD–dependent acetaldehyde dehydrogenase activity from *Alcaligenes eutrophus*," *Eur. J. Biochem.* 167:541–548 (1987).

Liebergesell, M. et al., "Purification and characterization of the poly(hydroxyalkanoic acid) synthase from *Chromatium vinosum* and localization of the enzyme at the surface of poly(hydroxyalkanoic acid) granules," *Eur. J. Biochem.* 226:71–80 (1994).

Murphy, D.J., "Structure, function and biogenesis of storage lipid bodies and oleosins in plants," *Prog. Lipid Res.* 32:247–280 (1993).

Peoples, O.P. and Sinskey, A.J., "Poly–β–hydroxybutyrate (PHB) biosynthesis in *Alcaligenes eutrophus* H16. Identification and characterization of the PHB polymerase gene (phbC)," *J. Biol. Chem.* 264:15298–15303 (1989).

Pieper, U. and Steinbüchel, A., "Identification, cloning and sequence analysis of the poly(3–hydroxyalkanoic acid) synthase gene of the Gram–positive bacterium *Rhodococcus ruber*," *FEMS Microbiol. Lett.* 96:73–80 (1992).

Pieper–Fürst, U. et al., "Purification and characterization of a 14–kilodalton protein that is bound to the surface of polyhydroxyalkanoic acid granules in *Rhodococcus ruber*," *J. Bacteriol.* 176:4328–4337 (1994).

(List continued on next page.)

*Primary Examiner*—Douglas W. Robinson
*Assistant Examiner*—Amy J. Nelson
*Attorney, Agent, or Firm*—Gary M. Bond; Arnold, White & Durkee

[57] ABSTRACT

The N-terminal amino acid sequence of the polyhydroxyalkanoic acid (PHA) granule-associated $M_r$ 15,500 protein of *Rhodococcus ruber*, which is referred to as the GA14-protein, was analysed. The sequence revealed that the corresponding structural gene is represented by the open reading frame 3 encoding a protein with a calculated $M_r$ 14,175 which was recently localized downstream of the PHA synthase gene (Pieper, U., and A. Steinbüchel, 1992. *FEMS Microbiol. Lett.* 96: 73–80). A recombinant strain of *Escherichia coli* XL1-Blue carrying the hybrid plasmid (pSKXA10*) with ORF3 overexpressed the GA14-protein. The GA14-protein was subsequently purified in a three-step procedure including chromatography on DEAE-Sephacel, Phenyl-Sepharose CL-4B and Superose 12. Determination of the molecular weight by gel filtration as well as electron microscopic studies make a tetrameric structure of the recombinant, native GA14-protein most likely. Immunoelectron microscopy demonstrated a localization of the GA14-protein at the periphery of PHA granules as well as close to the cell membrane in *R. ruber*. Investigations of PHA-leaky and PHA-negative mutants of *R. ruber* indicated that the expression of the GA14-protein depended strongly on PhA synthesis.

5 Claims, 13 Drawing Sheets

OTHER PUBLICATIONS

Schubert, P. et al., "Cloning of the *Alcaligenes eutrophus* genes for synthesis of poly–βhydroxybutyric acid (PHB) and synthesis of PHB in *Escherichia coli,*" *J. Bacteriol.* 170:5837–5847 (1988).

Schubert, P. et al., "Genes involved in the synthesis of poly(β–hydroxyalkanoic acid) in *Alcaligenes eutrophus,*" *DECHEMA Biotechnology Conferences*, vol. 3, Part A, VCH Weinheim, Federal Republik of Germany, pp. 433–436 (1989).

Schubert, P. et al., "Molecular analysis of the *Alcaligenes eutrophus* poly(3–hydroxybutyrate) biosynthetic operon: identification of the N–terminus of poly(3–hydroxybutyrate) synthase and identification of the promoter,"*J. Bacteriol.* 173:168–175 (1991).

Slater, S.C. et al., "Cloning and expression in *Escherichia coli* of the *Alcaligenes eutrophus* H16 poly–β–hydroxybutyrate biosynthetic pathway," *J. Bacteriol.* 170:4431–4436 (1988).

Steinbüchel, A. et al., "Considerations on the structure and biochemistry of bacterial polyhydroxyalkanoic acid granules and introducing the terms GAP and phasin," Lecture presented at the International Symposium on Bacterial Polyhydroxyalkanoates (ISBP '94) in Montreal (Aug. 15, 1994).

Steinbüchel, A. et al., "Molecular basis for biosynthesis and accumulation of polyhydroxyalkanoic acids in bacteria," *FEMS Microbiol. Rev.* 103:217–230 (1992).

Steinbüchel, A. and Schlegel, H.G., "Physiology and molecular genetics of poly(β–hydroxyalkanoic acid) synthesis in *Alcaligenes eutrophus,*" *Mol. Microbiol.* 5:535–542 (1991).

Timm, A. and Steinbüchel, A., "Formation of polyesters consisting of medium–chain–length 3–hydroxyalkanoic acids from gluconate by *Pseudomonas aeruginosa* and other fluorescent pseudomonads," *Appl. Environ. Microbiol.* 56:3360–3367 (1990).

Valentin, H.E. and Steinbüchel, A., "Application of enzymatically synthesized short–chain–length hydroxy fatty acid coenzyme A thioesters for assay of polyhydroxyalkanoic acid synthases," *Appl. Microbiol. Biotechnol.* 40:699–709 (1994).

Stam M, et al. "The silence of genes in transgenic plants." Ann. Bot. 79: 3–12, 1997.

Koziel MG, et al. "Optimizing expression of transgenes with an emphasis on post–transcriptional events." Plant Mol. Biol. 32: 393–405, 1996.

Smith CJS, et al. "Antisense RNA inhibition of polygalacturonase gene expression in transgenic tomatoes." Nature 334: 724–726, Aug. 25, 1988.

Pieper–Furst U, et al. "Purification and characterization of a 14–kilodalton protein that is bound to the surface of polyhydroxyalkanoic acid granules in *Rhodococcus ruber.*" J. Bacteriol. 176: 4328–4337, Jul. 1994.

```
                                        1.0-kbp XhoI-ApaI genomic fragment
       MCS      XhoI       S/D      Stop
...ATGACC...TCGACCTGAGG...ACGGAAGGAAGCGCATGACCACCGCCAAGACCCGGTCGACGCCGCGTGCCAA    (SEQ ID NO:2)
         (SEQ ID NO:1)

M  T    S   T   S   R     T   E   Q   G   T   P   *
                           (SEQ ID NO:5)   (SEQ ID NO:6)

```
                              MCS'
                       ┌──────────────────┐
             Stop          ApaI
GACCACCGGCCGACGCCGCCAAGGC...CTCCTCAAGTGA...CTGGACTGGGCCCGGTACC...

(SEQ ID NO:3)          (SEQ ID NO:4)

T   T   A   D   A   A   K   A     (SEQ ID NO:7)

(T) (T) A (D  A) A (K)              (SEQ ID NO:8)
```

FIG. 1C-3

US3
XhoI
5'-ccgCTCGAGGATGCTCCGGGTACG-3'

DS3
ApaI  Stop
5'-tttgggccctcaCTTCTCCTGCAGGTCGAGCAGGCTC-3'

DS3a
ApaI  Stop
5'-tttgggccctcaCTCCCGGGGCGAAGGAGACCTGCG-3'

DS3aI
ApaI  Stop
5'-tttgggccctcaGACCCAGCCGACGGGGCTGGCGG-3'

DS3aII
ApaI  Stop
5'-tttgggccctcaCTTGGTGAGGTCCTCGACCCAGC-3'

CTerUS
BamHI
5'-tttggatccCTGCCTCCGCCAGCCCGTC-3'

CTerDS
BamHI  EcoRV  Stop
5'-tttggatccgatatcTCACTTGAGGAGGATCGCGGGGCGG-3'

FIG. 6B

GRANULE-ASSOCIATED PROTEINS AND METHODS FOR THEIR USE IN POLYHYDROXYALKANOATE BIOSYNTHESIS

RELATED U.S. APPLICATION DATA

Continuation of Ser. No. 08/598,175, filed Feb. 7, 1996, now abandoned, which is a continuation of Ser. No. 08/500,735, filed Jul. 11, 1995 now abandoned.

FIELD OF THE INVENTION

This invention relates to the production of polyhydroxyalkanoate.

BACKGROUND OF THE INVENTION

Poly-3-hydroxybutyrate is a linear polyester of D(−)-3-hydroxybutyrate. It was first discovered in *Bacillus megaterium* in 1925. Polyhydroxybutyrate accumulates in intracellular granules of a wide variety of bacteria. The granules appear to be membrane bound and can be stained with Sudan Black dye. The polymer is produced under conditions of nutrient limitation and acts as a reserve of carbon and energy. The molecular weight of the polyhydroxybutyrate varies from around 50,000 to greater than 1,000,000, depending on the microorganisms involved, the conditions of growth, and the method employed for extraction of the polyhydroxybutyrate. Polyhydroxybutyrate is an ideal carbon reserve as it exists in the cell in a highly reduced state, it is virtually insoluble, and exerts negligible osmotic pressure.

Polyhydroxybutyrate and related polyhydroxyalkanoates, such as poly-3-hydroxyvalerate and poly-3-hydroxyoctanoate, are biodegradable theremoplastics of considerable commercial importance. The term "polyhydroxyalkanoate" OR "PHA" as used hereinafter includes copolymers of polyhydroxybutyrate with other polyhydroxyalkanoates such as poly-3-hydroxyvalerate.

Polyhydroxyalkanoate is biodegradable and is broken down rapidly by soil microorganisms. It is theremoplastic (it melts at 180° C.) and can readily be moulded into diverse forms using technology well-established for the other thermoplastics materials such as high-density polyethylene which melts at around the same temperature (190° C.). The material is ideal for the production of biodegradable packaging which will degrade in landfill sites and sewage farms. The polymer is biocompatible, as well as biodegradable, and is wall tolerated by the mammalian, including human, body, its degradation product, 3-hydroxybutyrate, is a normal mammalian metabolite. However, polyhydroxyalkanoate degrades only slowly in the body and its medical uses are limited to those applications where long term degradation is required.

Polyhydroxyalkanoate, produced by the microorganism *Alcaligenes eutrophus*, is manufactured, as a copolymer with of polyhydroxybutyrate and polyhydroxyvalerate, by Zeneca Limited and sold under the Trade Mark BIOPOL. It is normally supplied in the form of pellets for thermoprocessing. However, polyhydroxyalkanoate is more expensive to manufacture by existing methods than, say, polyethylene. It is, therefore, desirable that new, more economic production of polyhydroxyalkanoate be provided.

Our International Patent Application WO 92/19747 relates to the production of polyhydroxyalkanoate in plants, specifically in the seed of oil-producing plants.

There are numerous publications in the patent and scientific literature relating to the expression of PHA in microorganisms.

SUMMARY OF THE INVENTION

An object of the present invention is to provide materials and a method for improving the expression of polyhydroxyalkanoate in transgenic organisms which are capable of producing polyhydroxyalkanoate.

According to the present invention there is provided a gene specifying a polyhydroxyalkanoate polymer granule binding protein.

The said protein may be the protein designated GA14, isolated from *Rhodococcus ruber* or any other protein having analogous function isolated from another source thereof. A partial deduced amino acid sequence of GA14 from *Rhodococcus ruber* is given in FIG. 1(c) herewith. There is no reason to believe that proteins of similar function will not be found in other organisms which naturally produce PHA.

The function of proteins of the GA14 type is to influence granule size and number. It may be that producing a large number of small size polymer granules will result in a higher yield of polymer than a smaller number of larger sized granules. On the other hand, isolation of the larger granules may be simpler.

The invention also provides a transgenic organism adapted for the production of polyhydroxyalkanoate comprising a recombinant genome which contains genes encoding enzymes necessary for catalysing the production of polyhydroxyalkanoate together with gene regulatory sequences for controlling expression of the said genes characterised in that said genome contains a gene specifying a polymer granule binding protein.

The polymer granule binding protein may be GA14 or an equivalent thereof.

The transgenic organism may be a bacterium or a plant.

The genes encoding the enzyme or enzymes necessary for the catalysis of polyhydroxyalkanoate production may be isolated from a microorganism, such as *Alcaligenes eutrophus*, which is known to produce polyhydroxyalkanoate.

The present invention is concerned with a protein which we designate GA14 which has the ability to bind to granules of PHA which are synthesised within cells of organisms which have the requisite synthesis machinery for producing PHA. The presence or absence of the GA14 protein affects the size and number of the PHA granules. Control of granule size and number is important in industrial production of this biopolymer in order to optimize processing parameters such as those of the extraction step.

BRIEF DESCRIPTION OF THE DRAWINGS

FIGS. 1A, 1B, 1C1, 1C2, 1C3. Construction of the hybrid plasmid pSKXA10* and sequence data related to the expression of GA14-protein. (a) PHA synthase gene locus of *R. ruber*; (b) detailed structure of the 1.0-kbp XhoI-ApaI-fragment and its location in the MCS of pBluescript SK⁻ yielding pSKXA10*; X, 32 bp of the 3'-region of phaC$_{Rr}$; (C-1 to C-3) depiction of the putative lacZ-fusion gene and of ORF3. The deduced amino acid sequences are partially shown in the one-letter abbreviation code below the nucleotide sequence; the N-terminal amino acid sequence of the GA14-protein from granule preparations as determined by Edman degradation is marked in bold letters.

FIG. 2. Diagram illustrating the PHA content of *R. ruber* wild type and of mutants; the PHA fraction of the cellular dry matter is indicated on top if the columns.

FIGS. 6A–6B. Construction of truncated forms of phaP$_{Rr}$ and of a DNA fragment containing the 3'-terminal region of phaP$_{Rr}$ by PCR. (a) Relevant part of the nucleotide sequence of the 1.0-kbp XhoI-ApaI-fragment of pSKXA10* containing phaP$_{Rr}$. The deduced amino acid sequence of GA14-protein (SEQ ID NOS:14–15) is partially shown above the nucleotide sequence (SEQ ID NOS:10–13) in the one-letter code. The C-terminal hydrophobic domains HD1 and HD2 are underlayed. PCR-primers (SEQ ID NOS:16–22) used to construct truncated forms of phaP$_{Rr}$ and the product containing the 3'terminal region of phaP$_{Rr}$ that encodes the C-terminus of GA14-protein, are depicted as arrows, S/D, putative ribosome binding site. (b) Nucleotide sequence of the PCR-primers (SEQ ID NOS:16–22). Homologous parts to pSKXA10* are shown in capital letters, non-homologous parts are shown in small letters. Original or additional stop codons are underlayed. Restriction sites are underlined.

DETAILED DESCRIPTION OF THE INVENTION

Figure 1A:
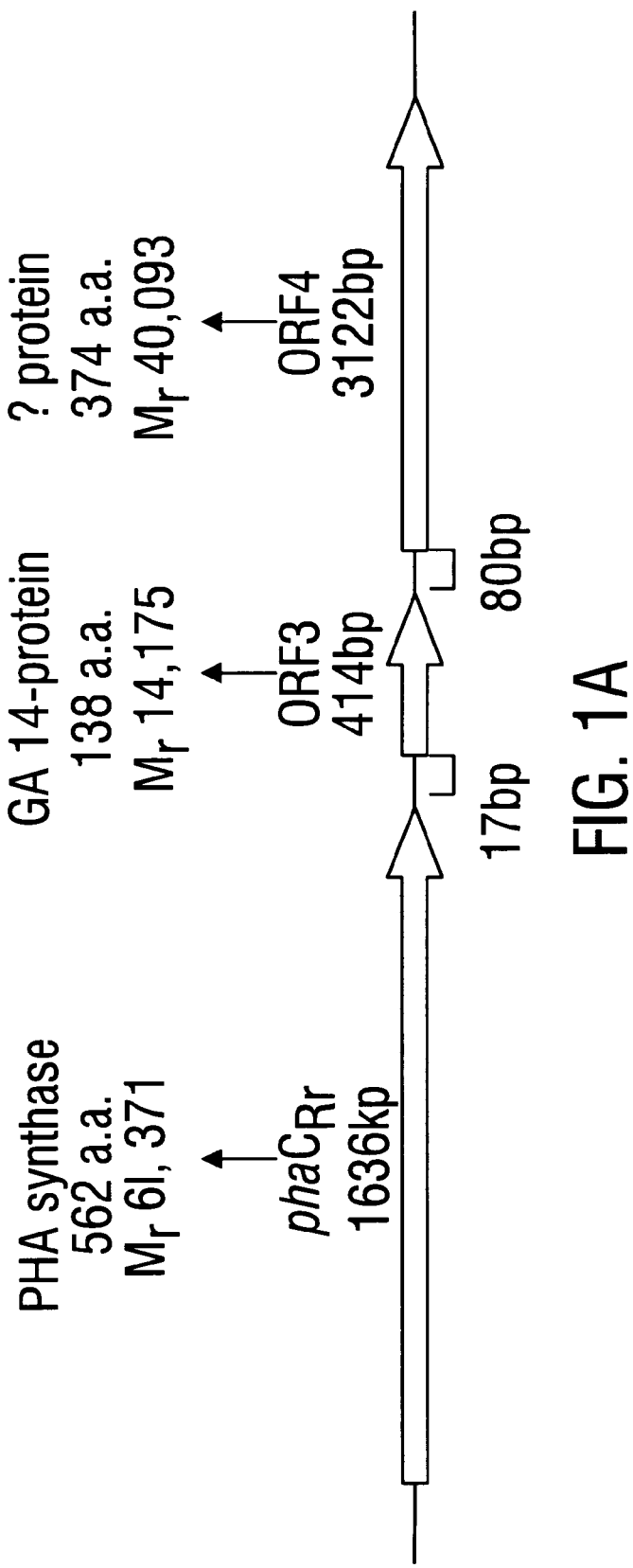

The N-terminal amino acid sequence of the GA14 protein of *Rhodococcus ruber* revealed that the corresponding structural gene is represented by open reading frame 3 (ORF3) encoding a protein with a calculated M$_r$ of 14,175 which we had previously localised downstream of the PHA synthase gene (35).

This invention is founded on our analysis of PHA-biosynthesis in *R. ruber* at the molecular level. The analysis revelaed a genomic fragment containing the genes for PHA synthase and a second granule associated protein, which we refer to as GA14. Since the structural gene of the GA14 protein maps downstream of the PHA synthase gene, and since the GA14 protein represents the major of four granule-associated proteins, an important function of this protein for the biosynthesis of PHA is indicated. A non-specific association of the GA14 protein to the PHA granules can be excluded. Immunological experiments with the wild-type as well as PHA-leaky and PHA-negative mutants of *R. ruber* indicated a positive correlation between the expression of the GA14 protein and the PHA content.

Recently, the coryneform bacterium *Rhodococcus ruber* NCIMB 40126 was found to accumulate a copolyester of 3-hydroxybutyric acid and 3-hydroxyvaleric acid from single unrelated carbon sources (13). Molecular analysis identified the PHA synthase gene, ORF3 encoding the GA14 protein, and ORF4 that codes for a protein of unknown function (35). N-terminal amino acid analysis of proteins, which were co-purified with the polymer granules, identified the PHA sunthase and the GA14 protein as PHA granule-associated proteins in *R. ruber*. Analysis of the primary sequence of the GA14 protein revealed two domains consisting of ten and nine hydrophobic or amphihilic amino acids, respectively, close to the C-terminus. These two domains are responsible for the anchoring of the GA14 protein in a phospholipid monolayer surrounding the PHA granule core. Expression of such domains in a transgenic organism in association with another protein to binding of that protein to PHA polymer granules.

Polyhydroxyalkanoic acids (PHA) are synthesized by many bacteria and function as an intracellular carbon and energy storage compound (1.48). Inside the cell the polyesters occur in granules which also contain proteins and lipids as described for *Bacillus megaterium* (11). PHA are considered as substitutes for conventional plastic materials due to their physical properties and biodegradability. A copolyester of 3-hydroxybutyrate and 3-hydroxyvalerate (P[3HB-co-3HV]) is already produced by ZENECA Bio-Products with *Alcaligenes eutrophus* (15). The PHA-biosynthesis genes of many bacteria have been analysed (50), and four basic biosynthetic pathways are discussed (48). The biosynthesis of poly(3-hydroxybutyric acid) (PHB) in *A. eutrophus* has been studied in most detail (for reviews see 1, 48, 49). Following the condensation of two molecules of acetyl-CoA to acetoacetyl-CoA by a 3-ketothiolase (EC 2.3.1.9), an NADPH-dependent acetoacetyl-CoA reductase (EC 1.1.1.36) catalyzes the reduction to D-(−)-3-hydroxybutyryl-CoA that is the substrate of the polymerizing enzyme PHB synthase. The structural genes of these enzymes are organized in one single operon.

Recently, biosynthesis of the copolymer P(3HB-co-3HV) from single, unrelated carbon sources by several coryneform bacteria such as *Rhodococcus ruber* ATCC 40126 was described (13). Molecular analysis of the biosynthesis of PHA in *R. ruber* had identified the clone pRPS2o which restored the ability for PHB biosynthesis in the PHB-negative mutant PHB⁻4 of *A. eutrophus* H16 (35). The hybride plasmid pRPS2o contained a 6.9-kbp genomic DNA-fragment of *R. ruber*, and sequence analysis revealed the PHA synthase structural gene (phaC$_{Rr}$) and two additional open reading frames (ORF3 and ORF4) with unknown function (FIG. 1a). Furthermore, separation of granule associated proteins of *R. ruber* in an SDS-polyacrylamide gel had exhibited four major bands representing proteins of M$_r$ 61,000, M$_r$ 42,000, M$_r$ 35,000 and M$_r$ 15,500 (35). N-terminal amino acid sequence analysis identified the M$_r$ 61,000 protein as the PHA synthase (35). In this study, we identified the granule-associated M$_r$ 15,500 protein as the translation product of ORF3 which is located downstream of the PHA synthase gene. This protein was purified and characterized, and specific antibodies were raised against this protein in order to contribute to the knowledge of its function in the biosynthesis of PHA and in the assembly of PHA granules in *R. ruber*.

EXAMPLES

Bacterial strains, plasmids and growth conditions. *Rhodococcus ruber* NCIMB 40126 (9), *Escherichia coli* XL1-Blue (5), and the pBluescript plasmids (Stratagene GmbH, Heidelberg, Germany) were used in this study. *R. ruber* was cultivated for 24 h at 30° C. in thiamine-supplemented mineral salts medium (MSM; 43) which was inoculated with a 24 hours Lurai-Bertani (LB)-preculture (40). To stimulate PHA accumulation, the concentration of ammonium chloride was reduced to 0.05% (wt/vol). *E. coli* was grown at 37° C. in LB-medium.

Quantitative and qualitative analysis of PHA. PHA were converted to the methyl esters of constituent hydroxyalkanoic acids which were analysed by gas chromatography as described elsewhere (3, 52).

Chemical mutagenesis and isolation of mutants defective in the accumulation of PHA. The mutagenesis with sodium nitrite was done essentially as described by Kaudewitz (20). The N-methyl-N'-nitro-N-nitroso-guanidine (NMG)-mutagenesis followed a method of Schlegel et al. (42). After mutagenesis cells were collected by centrifugation (2,800× g, 10 minutes, 4° C.), washed twice in 0.9% (wt/vol) NaCl and resuspended in 10 ml MSM with 0.05% (wt/vol) ammonium chloride and 0.2% (wt/vol) sodium valerate. Cells were cultivated at 30° C. for 24 hours, harvested, washed, and the cell density was adjusted to an optical density (OD) at 436 nm of 10. Mutants defective in the accumulation of PHA were enriched in Percoll density gradients (33). This method utilizes the observation that PHA-free mutants of *A. eutrophus* have a lower density than PHA-containing cells (33). In order to obtain clearly visible differences between *R. ruber* wild type cells and the mutants, as described, e.g., for the wild type and PHA-negative mutants of *A. eutrophus* (42), the conditions to achieve a maximum level of polymer accumulation were optimized. Since previous studies has demonstrated that *R. ruber* accumulated PHA up to 90% of cellular dry matter from sodium valerate (13), cells of each fraction above the wild type band were plated on MSM containing 0.02% (wt/vol) sodium valerate and incubated at 30° C. for 2 days. PHA-leaky and PHA-negative mutants could be distinguished from colonies of the wild type on the basis of their transparent reddish colony phenotype.

Electrophoresis of proteins. Samples were resuspended in gel loading buffer (0.6% wt/vol SDS, 1.25% vol/vol β-mercaptoethanol, 0.25 mM EDTA, 10% vol/vol glycerol, 0.001% wt/vol bromophenol blue, 12.5 mM Tris/HCl, pH 6.8) and were separated in 11.5% (wt/vol) sodium dodecyl sulphate polyacrylamide gels (SDS-PAG) as described by Laemmli (24). Proteins were stained with Coomassie Brilliant Blue R250 (56).

Preparation of PHA granules and analysis of the N-terminal amino acid sequence of the GA14-protein. PHA granules of *R. ruber* were isolated by density gradient centrifugation as described previously (35). The associated proteins were released from the granule core by resuspension in gel loading buffer and were separated in an SDS-PAGE. For determination of the N-terminal amino acids of the GA14-protein, the protein was extracted from the gel following a method described by Weber and Osborn (56). For removal of SDS, the freeze-dried proteins were precipitated with acid acetone (21). The N-terminal amino acid sequence was determined by automated Edman degradation.

Isolation, manipulation and transformation of DNA. Isolation of plasmid DNA, agarose gel electrophoresis of DNA, and use of restriction endonucleases and of ligase were done by standard procedures (40). DNA was extracted from agarose following the method described by Vogelstein and Gillespie (55). *E. coli* XL1-Blue was transformed using the $CaCl_2$ method (40).

Overexpression and purification of the GA14-protein. A 1.0-kbp XhoI-ApaI-fragment containing the gene for the GA14-protein of *R. ruber* (35) was ligated to pBluescript SK⁻ DNA which has been treated with XhoI and ApaI. Ligation products were transformed into *E. coli* XL1-Blue, and transformants harboring the construct (pSKXA10*) were used to inoculate 10 ml LB-medium containing 12.5 µg tetracycline (Tc) and 75 µg ampicillin (Ap) per ml. After incubation at 37° C. for 10 hours these precultures were transferred into 100 ml LB-medium containing 12.5 µg Tc per ml, 75 µg Ap per ml and 1 mM isopropyl-β-D-thiogalactopyranoside (IPTG). After 20 hours cultivation at 37° C., a total of 4 g of cells was collected from ten 100 ml cultures by centrifugation.

Cells were washed and resuspended in 25 ml 20 mM sodium phosphate buffer (pH 6.5). All steps were carried out at 4° C. in this buffer, and proteins were eluted from the columns at a flow rate of 0.5 ml/minute. Cells were broken by twofold French Press passage ($110 \times 10^6$ Pa), and cell debris and membranes were removed from the crude extract by centrifugation (100,000×g, 1 hour, 4° C.). The supernatant (25 ml) was dialysed 2 hours against 2 l of buffer and applied onto a column (2.6 cm×12.2 cm, 65 ml bed volume) of DEAE-Sephacel (Pharmacia Biosystems GmbH, Freiburg, Germany). The GA14-protein eluted in the wash fractions. Those fractions containing GA14-protein were identified by SDS-polyacrylamide gel electrophoresis (SDS-PAGE), pooled and concentrated 15-fold in a Diaflow chamber using a PM10 Membrane (Amicon, Witten, Germany). Six mg of protein (1.25 ml) were loaded onto a column (1.6×9.0 cm, 18 ml bed volume) of Phenyl-Sepharose CL-4B (Pharmacia Biosystems GmbH, Freiburg, Germany). Again, the protein eluted in the wash fractions and 41 ml containing GA14-protein were collected and concentrated 80-fold using a Diaflow chamber (see above) as well as a Centricon 10 concentrator (Amicon, Witten, Germany). From this concentrate 250 µl (0.6 mg protein) were applied onto a Superose 12 FPLC column (Pharmacia Biosystems GmbH, Freiburg, Germany) equilibrated with buffer. Buffer (1.5 ml) containing GA14-protein were collected and concentrated using a Centricon 10 concentrator.

Preparation and purification of antibodies. The antigen (500 µg in 500 µl 20 mM sodium phosphate, pH 6.5) was mixed with complete Freund's adjuvant (500 µl) and injected subcutancously along the back of a rabbit (New Zealand, female, 2.5 kg). The booster injection using the same amount of antigen mixed with incomplete Freund's adjuvant was done after 4 weeks. After additional 11 days the rabbit was bled. In order to obtain monospecific antibodies against the GA14-protein, the antiserum was subjected to an affinity purification following a modification of the method described by Olmsted (32). Approximately 3.5 mg of the antigen were separated in an SDS-PAGE and blotted onto a nitrocellulose BA83 membrane (pore size 0.2 µm, Schleicher & Schuell, Dassel, Germany) using a Semi-dry Fast Blot B33 apparatus (Biometra, Göttingen, Germany). The membrane was stained with 0.2% (wt/vol) Ponceau S (Sigma, Deisenhofen, Germany) in 3% (wt/vol) trichloroacetic acid, and the region harboring the GA14 protein was cut out. Free protein binding sites on this membrane were blocked with 2.5% (wt/vol) skim milk in phosphate-buffered saline (PBS) (10 mM potassium phosphate, pH 7.2, 0.5%, wt/vol NaCl, 0.05% wt/vol Tween 20) at 37° C. for 1 hour. The membrane was incubated with 3 ml of the antiserum at room temperature for 3 hours. After three washing steps for 10 minutes with PBS, GA14-specific antibodies were eluted twice for 2 minutes with 2 ml elution buffer (5 mM glycine, pH 2.3, 0.5 M NaCl, 0.05% wt/vol Tween 20). The antibody solution (approximately 30 μg/ml) was neutralized with 1 M potassium phosphate (pH 8.0) and after addition of 1% (wt/vol) bovine serum albumin, the solution was stored at −20° C.

Western blotting. Proteins were separated in an SDS-PAG (11 cm×10 cm×1 mm) and blotted onto nitrocellulose membrane (see above). Free binding sites were blocked with 2.5% (wt/vol) skim milk in PBS at 37° C. for 1 hour. Antibodies were diluted one hundred-fold in PBS containing 0.5% (wt/vol) Tween 20 and incubated with the immobilized antigen at room temperature for 3 hours. Following three washing steps (each 10 minutes in PBS), the membrane was transferred into a solution of anti-rabbit IgG-alkaline phosphatase conjugate (Sigma, Deisenhofen, Germany) in PBS containing 0.5% (wt/vol) Tween 20. After 1 hour incubation at room temperature the membrane was washed three times in PBS and once in reaction buffer (0.1 M Tris/HCl, pH 8.8, 0.1 M NaCl, 5 mM $MgCl_2$). Bound antibodies were detected with 22 μl of a solution of nitro blue tetrazolium (NBT, 75 mg per ml in 70% vol/vol dimethylformamide) and 17 μl of a solution of 5-bromo-4-chloro-3-indolylphosphate (BCIP, 50 mg per ml in 100% vol/vol dimethylformamide) in 20 ml reaction buffer.

Molecular weight determination. The relative molecular mass ($M_r$) of the GA14-protein was determined by gel filtration on a Superose 12 FPLC column (Pharmacia Biosystems GmbH, Freiburg, Germany) that was equilibrated with 20 mM sodium phosphate buffer, pH 6.5. Ribonuclease A from bovine pancreas ($M_r$ 13,700), chymotrypsinogen A from bovine pancreas ($M_r$ 25,000), ovalbumin from hen egg ($M_r$ 43,000) and albumin from bovine serum ($M_r$ 67,000) were used as standard proteins (Pharmacia Biosystems GmbH, Freiburg, Germany).

Electron microscopic studies. Negatively stained samples of the GA14-protein were prepared from a solution of 10 to 25 μg protein per ml (54), using 4% (wt/vol) aqueous uranyl acetate, pH 4.8, as stain (29). For post-embedding immunogold labeling of the GA14-protein, cells and PHA granules were washed twice with 50 mM potassium phosphate (pH 7.0) and were subsequently fixed with a mixture of 0.3% (vol/vol) glutaraldehyde and 0.2% (wt/vol) paraformaldehyde in the buffer mentioned above (39). This fixation method preserved both the ultrastructure of the cells and the antigenicity of the GA14-protein, as controlled by Western blotting. The samples were embedded in Lowicryl K4M (Lowi, Waldkraiburg, Germany) as described (39), however, methanol instead of ethanol was used for dehydration. Ultrathin sections were mounted onto formvar-covered nickel grids, and free protein binding sites were blocked with skim milk (7). The samples were incubated overnight at 4° C. with a series of different dilutions of the primary antibody. Sections were washed by a mild spray PBS-Tween (50 mM potassium phosphate, 0.9% wt/vol NaCl, 0.05% vol/vol Tween 20, pH 6.9) and subsequent incubations on drops of PBS-Tween (3×3 minutes). The grids were then incubated with a series of dilutions of Goat-anti-rabbit-IgG gold complex (GARG, Dakopatts, Hamburg, Germany) at room temperature for 2 hours. Afterwards, the sections were rinsed as described above followed by a washing step in water. Post-staining was performed in 4% (wt/vol) aqueous uranyl acetate, pH 4.5 for 3 to 5 minutes. The specificity of the labeling was demonstrated by a control experiment using only the GARG complexes. For metal shadowing the sections were coated with platinum-carbon evaporated at an angle of 30° (Metal shadowing apparatus, type EPA 100, Leybold-Heraeus, Hanau, Germany). Micrographs were taken on a Philips EM 301 electron microscope at 80 kV acceleration voltage. Magnifications were calibrated with a cross-linked grating replica (Balzers Corp., Liechtenstein).

Identification of the GA14-protein. Analysis of the N-terminus of the granule-associated $M_r$ 15,500 protein, the predominant representative of four proteins bound to isolated granules of R. ruber (35), yielded the following amino acid sequence: ? ? A K (T) P V D A A (V) A K (T) (T) A (D) (A) A K (SEQ ID NO:8; question marks and parenthesis indicate unidentified or uncertain amino acids, respectively). It was in agreement with the amino acid sequence deduced from the nucleotide sequence of the 5'-region of ORF3, which maps downstream of the PHA synthase structural gene (pha$C_{Rr}$) (FIGS. 1a and 1c). The N-terminal methionine residue is probably removed in vivo. ORF3 comprised 414 bp and encoded a protein of 138 amino acids with a $M_r$ of 14,175 (FIG. 1a; 35). Subsequently, the ORF3-product will be referred to as GA14-protein.

Figure 1B:
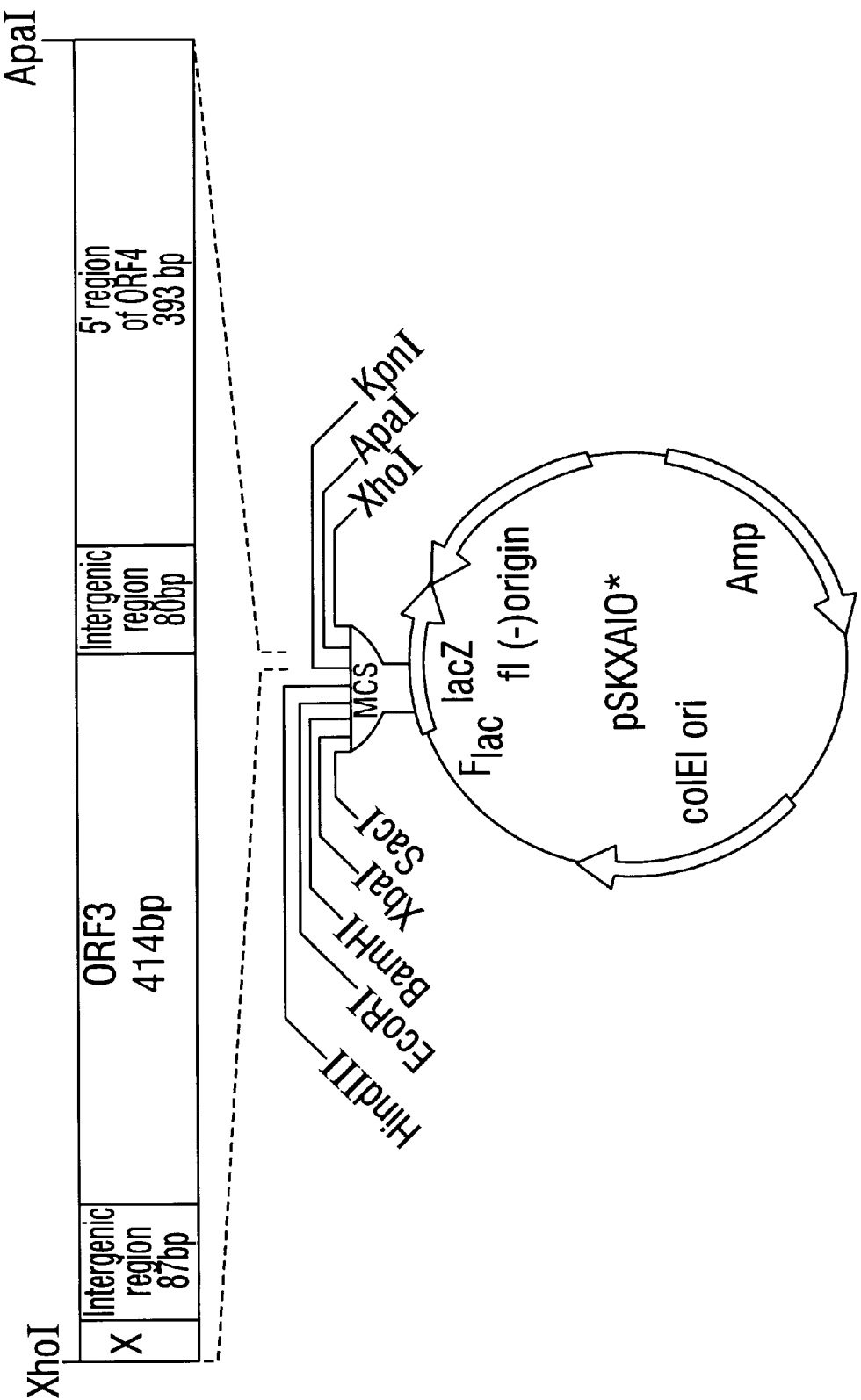

Construction of the hybrid plasmid pSKXA10* and overexpression of GA14-protein in E. coli. A 1.0-kbp XhoI-ApaI-subfragment of clone pRPS2o, which contained 32 bp of the 3'-region of pha$C_{Rr}$, an intergenic region of 87 bp, the entire ORF3, an intergenic region of 80 bp and 393 bp of the 5'-region of ORF4, was ligated into pBluescript SK to generate the hybrid plasmid pSKXA10* (FIG. 1b). By this construction a new open reading frame was obtained comprising the 5'-region of the β-galactosidase gene (lacZ) until the XhoI-site of the multi cloning site (144 bp), 32 bp of the 3'-region of pha$C_{Rr}$, the 87-bp-intergenic region upstream of ORF3 and the first nucleotide of ORF3. The stop condon (TGA) of this lacZ-fusion gene overlapped with the start condon (ATG) of ORF3 (FIG. 1c, containing nucleic acid SEQ ID NOS:1–4, encoding amino acid SEQ ID NOS:5–8). Cells of E. coli XL1-Blue (pSKXA10*) containing ORF3 downstream and colinear to the lac-promotor ($P_{lac}$) synthesized a protein with the same overexpression of this protein occurred. Cells of E. coli XL1-Blue containing (pKSAX10) containing ORF3 downstream and co-linear to the lac-promoter ($P_{lac}$) synthesized a protein with the same electrophoretic mobility as the GA14-protein. In the XL1-Blue containing pKSAX10—a construct of pBluescript KS⁻ and the 1.0-kbp XhoI-ApaI-fragment—with ORF3 downstream but in antilinear of ORF3 was under the control of $P_{lac}$. The proposed fusion protein composed of 88 amino acids and exhibiting a $M_r$ of 9,217 was not detected.

Purification of the GA14-protein. The purification of the GA14-protein started from 4 g wet cells of E. coli XL1-Blue (pSKXA10*) which had been cultivated in the presence of IPTG. The GA14-protein constituted approximately up to 10% of the total soluble protein in crude extracts as estimated from the electropherogram. Following dialysis the proteins were loaded onto a DEAE-Sephacel column. Due to an isoelectric point of 4.66 of the GA14-protein (see below), a buffer of pH 6.5 was choosen. It was expected that the native GA14-protein would have a negative net charge and would therefore bind to the anion exchange matrix. However, it was eluted in the wash fractions with high purity. The concentrated protein was than applied to a column of Phenyl-Sepharose CL-4B. Again, the GA14-protein did not bind to the column and was eluted in the wash fractions, whereas contaminating proteins were efficiently retained on the hydrophobic matrix. Subsequent gel filtration of a Superose 12 FPLC column yielded 830 μg GA14-protein. When this protein was subjected to Edman degradation, an N-terminal amino acid sequence (? ? A K ? P V D A A V A K) (SEQ ID NO:25) was obtained which corresponded to the amino acid sequence deduced from the nucleotide sequence of ORF3 (FIG. 1c). The protein that appeared below the GA14-protein in SDS polyacrylamide gels was a proteolytic fragment emerging during the purification as demonstrated by Western blotting (data not shown).

Properties of the GA14-protein. The relative molecular mass of the native GA14-protein, isolated from the recombinant E. coli strain, as determined by gel filtration on a Superose 12 FPLC column was 53,500±3,700 irrespective of the presence or absence of NaCl (0 to 1 M) during chromatography. Following negative staining of the native GA14-protein with uranyl acetate, electron micrographs showed particle projections of a size ranging from 7 to 12 nm in diameter and with 3 or 4 intensity maxima. These images can be interpreted as triangular and square projection of one type of tetrameric protein resulting from different orientations of the protein complex (29). We therefore concluded that the quaternary structure of the native GA14-protein in E. coli is a tetramer. Structures 3 nm in diameter were also frequently revealed; they may represent monomers of the GA14-protein which could result as products of partial decomposition taking place during the negative staining procedure. In addition, noticeable irregular structures with diameters of more than 12 nm occurred; these were interpreted as aggregates of a large number of GA14-protein molecules. The tendency of the GA14-protein to form aggregates may be the reason for irreversible precipitation of a part of the protein during the purification.

An absorption spectrum of the purified GA14-protein revealed only protein specific maxima at 214 nm and 280 nm and did not indicate the presence of cofactors. The isoelectric point of the GA14-protein was calculated to be 4.66 on the basis of the primary structure deduced from the nucleotide sequence of ORF3 using the program ISOELECTRIC of the GCG-package (6). This value was confirmed by isoelectric focussing (data not shown). Hitherto, no homologies of the GA14-protein to other proteins were detected by comparison of primary structures of proteins in the EMBL gene bank. Analysis of the amino acid sequence of the GA14-protein deduced from ORF3 (35) revealed that the GA14-protein is composed of 16 mol % of extremely hydrophobic (I, V, L), 29 mol % of hydrophobic (F, M, A), 24 mol % of amphiphilic (G, T, W, S, Y, P) and 31 mol % of hydrophilic amino acids (R, N, D, Q, E, H, K). No protein segment comprising 19 amino acids with amphiphilic and/or hydrophobic character was identified that could represent a typical bilayer membrane spanning part of a protein as described by Kyte and Doolittle (23). However, two segments of 10 and 9 hydrophobic and/or amphiphilic amino acids were detected between amino acid position 102 to 111 and 125 to 133 of the polypeptide, respectively (35). The length of each of these sections would be sufficient to span a phospholipid monolayer.

Rabbit antiserum raised against the GA14-protein showed cross reactivity with several other proteins from R. ruber (data not shown) presumably due to the use of complete Freund's adjuvant with cell material of Mycobacterium. After the antiserum was purified as described in materials and methods it was highly specific for the GA14-protein as demonstrated by Western blotting. Cross reactivity of the GA14-specific antibodies with PHA granule-associated proteins of A. eutrophus or C. vinosum strain D was not observed (results not shown).

Figure 2:
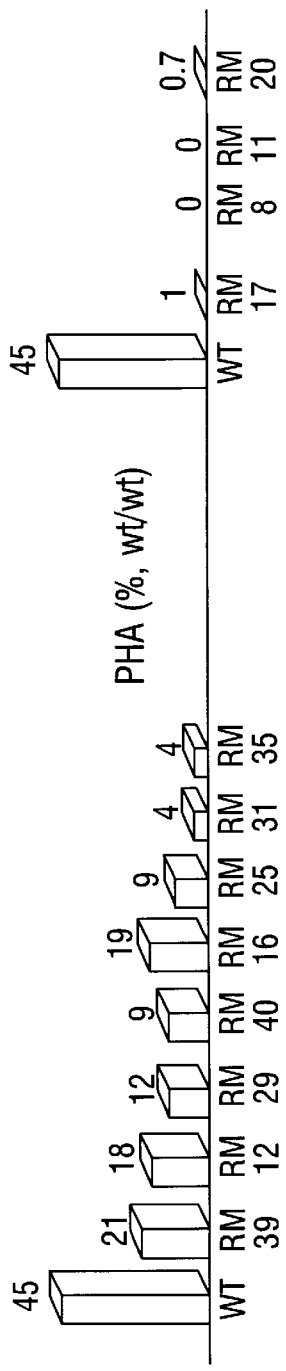

Isolation and characterization of mutant defective in the biosynthesis of PHA. Chemical mutagenesis and Percoll density gradient centrifugation were applied to obtain mutants of R. ruber which lack the ability to accumulate PHA (referred to as PHA-negative mutants) or which accumulate less PHA than the wild type (referred to as PHA-leaky mutants). The frequency of mutations varied between 0.5 and $3.5 \times 10^{-7}$ in different experiments. When glucose was used as the sole carbon source during cultivation for characterization of the mutants, cells of the wild type accumulated PHA up to 45% (wt/wt) of the cellular dry matter, whereas the PHA content in the mutant cells ranged from 0 to 21% (wt/wt) (FIG. 2). Significant alterations of the composition of the accumulated polyester, which consists of approximately 25 mol % 3-hydroxybutyric acid and 75 mol % of 3-hydroxyvaleric acid in the wild type (13), were not observed (data not shown).

Several mutants were analysed regarding the relationship between PHA accumulation and expression of the GA14-protein. Immunoblots clearly revealed a strong correlation between the amount of GA14-protein and the level of PHA synthesis in these cells (FIG. 2). The strongest immunoreaction was found with crude extracts of R. ruber wild type that accumulated 45% (wt/wt) of cellular dry weight. The PHA-leaky mutants RM39 and RM12 with a PHA content of 21 and 18% (wt/wt), respectively, showed slightly weaker reactions with the anti-GA14-antibody. With crude extracts of the PHA-leaky mutants RM29, RM40, RM16 and RM25 accumulating 9 to 19% (wt/wt) PHA only a faint immunoreaction was visible. The PHA-leaky mutants RM31, RM35, RM17 and RM20 with a PHA content between 0.7 and 4% (wt/wt) as well as the PHA-negative mutants RM8 and RM11 did not express any detectable GA14-protein according to Western blots of crude extracts derived from these cells.

Immunoelectron microscopic localization of the GA14-protein. The purified polyclonal antibodies directed against the GA14-protein (see above) were also used to localize the polypeptide in the cells at the ultrastructural level by immunoelectron microscopy. R. ruber cells were embedded in Lowicryl, and subsequently ultrathin sections were subjected to immunogold labeling. Surprisingly the decoration was confined to two distinct location within the cells of the wild type: first, the periphery of the PHA granules was strongly decorated while the interior of the granules remained unlabeled; second, the cytoplasmic side of the cell membrane also exhibited a substantial amount of gold label. Metal shadowing of the ultrathin sections confirmed that the entire surface of the granules was coated with GA14-protein. Metal shadowing of sections at a low angle allows to obtain information on the topology of sections and indicates that the surface of a section is not completely flat; rather, in those areas of the section where a cell is sectioned, this cell is somewhat elevated above the surrounding resin, and surfaces of PHA granules within these cells which are exposed at the surface of the section can be identified. With cells of the PHA-negative mutant R. ruber RM11 no specific label was observed (data not shown). This was in excellent agreement with the results obtained by Western blotting that indicated a lack of expression of the GA14-protein in this mutant (see above). To correlate these results with data of other biochemical and immunological experiments, which indicated that the GA14-protein was enriched during the purification of the PHA granules, we also subjected isolated granules to immunoelectron microscopy. Antibodies decorated the surface of isolated granules exactly like granules in whole cells. Occasionally some irregularly shaped objects were labelled. These most likely represent granules that were disrupted during the preparation. The high specificity of the immunogold labeling method employed here is demonstrated in the control sections that were incubated only with the Goat-anti-rabbit-IgG gold complexes.

It was also interesting to investigate the subcellular localization of the GA14-protein in the strain E. coli XL1-Blue (pSKXA10*) that was constructed for overexpression of this protein. Most of the cells exhibited strong decoration of their periphery indicating that the GA14-protein seems to have a strong tendency to bind to membraneous structures (data not shown). A substantial fraction of the cells was labeled rather uniformly throughout the whole cytoplasm (data not shown).

Discussion

Analysis of PHA-biosynthesis in R. ruber at the molecular level yielded a genomic fragment containing the genes for the PHA synthase and a second granule-associated protein, which is referred to as the GA14-protein. Since the structural gene of the GA14-protein maps downstream of the PHA synthase gene, and since the GA14-protein represents the major of four granule-associated proteins, an important function of this protein for the biosynthesis and/or the accumulation of PHA is most likely. An unspecific association of the GA14-protein to the PHA granules as described recently for lysozyme (25) can be excluded. Immunological experiments with the wild type as well as with PHA-leaky and PHA-negative mutants of R. ruber indicated a positive correlation between the expression of the GA14-protein and the PHA content. This could result from a mutation in a putative promotor upstream of the PHA synthase gene that prevents the transcription of the PHA synthase gene and ORF3. Promotor structures, however, have not yet been identified in the genus Rhodococcus, and therefore a clear statement about promotor structures in R. ruber is not possible at present. Putative transcriptional termination structures were identified upstream of the PHA synthase gene and downstream of ORF3, but not in the short intergenic region. Therefore, a transcription unit consisting of both genes is plausible. The analysis of a large number of mutants makes it very unlikely that all these mutants have the same kind of genotype that is characterized by a mutation in the putative promotor region. Therefore, the question is rather whether the GA14-protein is only expressed if PHA is synthesized, or whether PHA synthesis depends on the presence of the GA14-protein. Since no PHA synthase activity was detected in the PHA-negative mutants RM8 and RM11 as well as in the PHA-leaky mutants RM17 and RM20 (data not shown), which are characterized by an extremely low PHA content, the mutations had most probably occurred in the PHA synthase gene. Therefore, it is most likely that the capability for PHA synthesis was inhibited first in the mutants, and that subsequently the expression of the GA14-protein was prevented. To confirm this hypothesis, extended and detailed studies on the regulation of PHA biosynthesis in R. ruber including molecular analysis of the defects in PHA-negative and PHA-leaky mutants have to be done.

Figure 3A:
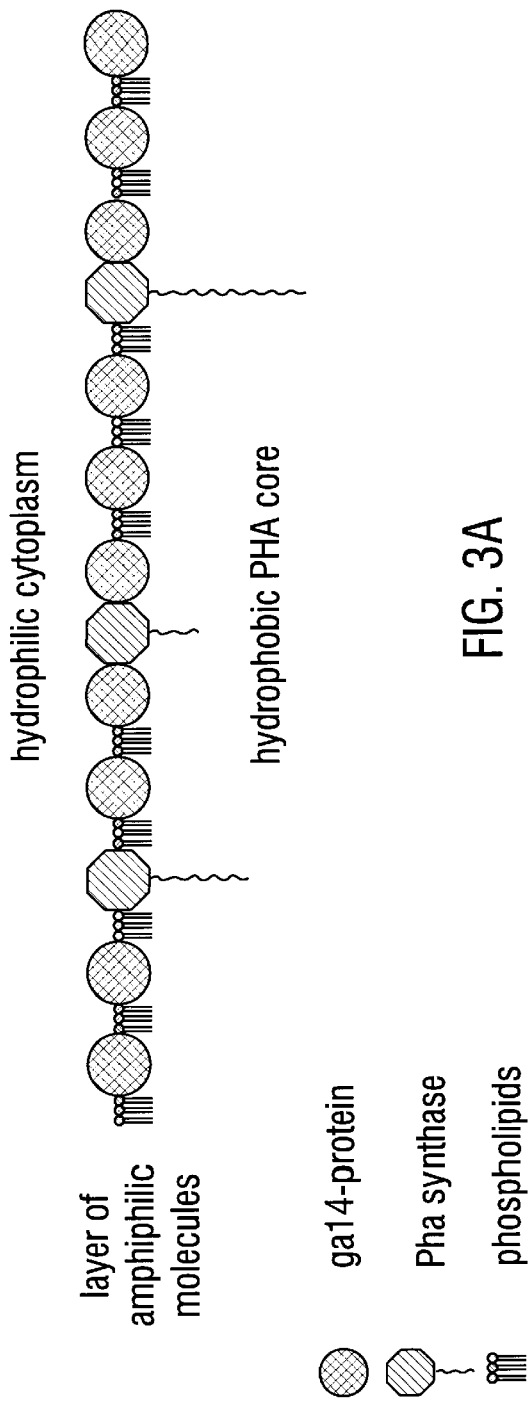
FIGS. 3A–3B. Model for the structure and composition of the PHA granule surface in *R. ruber* (A) and for the anchoring of the GA14-protein monomer (SEQ ID NO:9) in a phospholipid monolayer (B). The grouping of amino acids is according to Huang (16). The circle for the GA14-protein in (A) does not reflect the quaternary structure of the GA14-protein since this is not known for the native protein as it occurs in *R. ruber*.
Figure 3B:
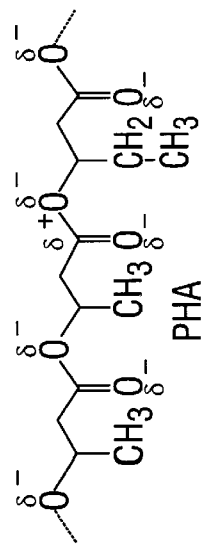

Immunoelectron microscopic studies localized the GA14-protein at the surface of PHA granules and at the cytoplasmic membrane of R. ruber as well as at the cytoplasmic membrane and in the cytoplasm of E. coli XL1-Blue (pSKXA10*) that overexpressed the GA14-protein. These results clearly demonstrated the tendency of the GA14-protein to bind to membraneous structures. However, the GA14-protein does not have a complete hydrophobic character as revealed by its solubility in the cytoplasm of E. coli, by its lacking affinity to the hydrophobic chromatography matrix Phenyl-Sepharose during purification, and by the amino acid composition. On the assumption that PHA granules are surrounded by a phospholipid monolayer rather than by a bilayer (28), an anchoring and positioning of the GA14-protein to the granule surface may be achieved by the two segments of hydrophobic and amphiphilic amino acids of the GA14-protein mentioned above (FIG. 3B). This hypothesis requires the expression of the GA14-protein as a monomer in R. ruber in contrast to the tetrameric structure determined for the recombinant protein in E. coli. Previous studies have revealed that PHB granules of Bacillus megaterium are composed of 97.7% PHB, 1.87% protein and 0.46% lipid (11). For PHB granules which have diameters ranging from 0.2 to 0.5 $\mu$m and which are surrounded by a phospholipid monolayer of 2 to 3 nm thickness (27), however, a phospholipid content of 2.5 to 6.0% (wt/wt) is required. This discrepancy between the calculated and the experimentally determined phospholipid content makes it likely that other amphiphilic molecules contribute considerably to the granule surface that separates the hydrophobic core of the PHA granules and the hydrophilic cytoplasm. Amphiphilic proteins may represent putative candidates which, together with phospholipid and the PHA synthase, occur at the surface of the PHA granules. Amphiphilic proteins have been recently found at the surface of oil bodies of seeds from plants (16). Therefore, we propose that the models of PHA granule assembly as described previously by several laboratories have to be modified by considering proteins which occur in addition to the PHA synthase at the surface of the granules. The latter enzyme has only a relatively low share in the composition of the granule-associated proteins (25, 35). In R. ruber the GA14-protein investigated in this study is probably the main component of the granule surface functioning as an amphiphilic protein in the interphase between the hydrophilic cytoplasm and the hydrophobic polyester molecules (FIG. 3A). In addition, it may also function as an anchor for the binding of additional proteins like, for instance, the PHA synthase.

Bacterial strains and plasmids. The Escherichia coli strain and plasmids used in this study are listed in Table 1.

Growth conditions and preparation of crude extract. Recombinant strains of E. coli XL1-Blue were grown for 12 hours at 37° C. in 10 ml LB medium (40) supplemented with 100 $\mu$g ampicillin and 12.5 $\mu$g tetracycline per ml. Two or ten ml of these precultures were used to inoculate 50 or 300 ml LB medium, respectively, containing 100 $\mu$g ampicillin and 12.5 $\mu$g tetracycline per ml and in addition 1% (wt/vol) glucose or 0.1 mM isopropyl-$\beta$-D-thiogalactopyranoside (IPTG) plus 0.2% (wt/vol) glucose. These cultures were incubated for 24 hours at 37° C. The growth was monitored using a Kleu-Summerson photometer (Filter No. 54, 520–580 nm). Cells were harvested by centrifugation (2,800×g, 10 minutes, 4° C.), washed and resuspended in 0.1 volumes of 10 mM Tris/HCl, pH 7.0. Cells were broken by a twofold French press passage (110×10$^6$ Pa), and soluble protein fractions were prepared from the resulting crude extracts by ultracentrifugation (100,000×g, 1 hour, 4° C.).

Preparation of native and artificial PHB granules; binding assays of proteins. Native PHB granules were isolated from cells of recombinant E. coli strains by loading approximately 3 ml crude extract onto discontinuous glycerol gradients (2 ml 88% vol/vol, and 5 ml 50% vol/vol, glycerol), which were centrifuged for 1 hour at 49,000×g and 4° C. PHB granules collected at the 88% to 50% interphase; they were removed from the gradient, pelleted (12,000×g, 20 minutes, 4° C.), washed and resuspended in 300 $\mu$l 10 mM Tris/HCl, pH 7.0.

The preparation of artificial PHB granules from *A. eutrophus* was performed as described by Jendrossek et al. (19). The binding assays with proteins were done according to Liebergesell et al. (26).

Protein determination and enzyme assays. Protein concentrations were determined as described by Bradford (2), β-Ketothiolase activity in the soluble protein fraction was measured in the thiolysis direction as described by Nishimura and coworkers (31). Activity of the NADPH-dependent acetoacetyl-CoA reductase in the soluble protein fraction was monitored by measuring the oxidation of NADPH (14). PHB synthase activity was determined spectroscopically in the crude extract according to Valentin and Steinbüchel (53). Activity of AcDH-II was monitored in the soluble protein fraction by measuring the initial rate of NAD reduction (18).

Quantitative and qualitative analysis of PHA. PHA were converted to the methyl esters of constituent hydroxyalkanoic acids which were analysed by gas chromatography as described elsewhere (3, 52).

Electrophoresis of proteins. Samples were resuspended in gel loading buffer (0.6% wt/vol SDS, 1.25% vol/vol β-mercaptoethanol, 0.25 mM EDTA, 10% vol/vol glycerol, 0.001% wt/vol bromophenol blue, 12.5 mM Tris/HCl, pH 6.8), and the proteins were separated in 10 to 15% (wt/vol) sodium dodecyl sulphate (SDS)-polyacrylamide gels as described by Laemmli (24). Proteins were stained with Coomassie Brilliant Blue R 250 (56).

Immunoblotting. Electrophoresis of proteins in SDS-polyacrylamide gels, blotting onto nitrocellulose membranes and the antibody reactions were done as described previously (36). Immunoglobulins directed against the GA14-protein of *R. ruber* were affinity purified (36). Antibodies directed against the acetaldehyde dehydrogenase II (AcDH-II) of *A. eunophus* were available from a previous study (18).

Electron microscopy. Postembedding immunogold labeling of the wild type and a truncated variant of the GA14-protein on ultrathin sections of recombinant *E. coli* XL1-Blue was done as described previously (36).

For demonstration of the granule size the cells were washed in 10 mM Tris, pH 7.0, 0.15 M NaCl and contrasted essentially as described previously (29). A 2% (wt/vol) aqueous solution of phosphotungstic acid neutralized with NaOH was used for negative staining.

Isolation, manipulation and transformation of DNA. Isolation of plasmid DNA, agarose gel electrophoresis of DNA and the use of restriction endonucleases, T4 DNA ligase, Klenow-fragment of DNA polymerase I as well as mung bean nuclease was done by standard procedures (40). DNA was extracted from agarose as described by Vogelstein and Gillespie (55). Preparation of frozen competent cells of *E. coli* XL1-Blue by the $RbCl/CaCl_2$ method and their use for transformation was done according to protocol 3 described by Hanahan (12).

Polymerase chain reaction (PCR). 1 μM of each oligonucleotide, 200 μM of each dNTP (Stratagene), 250 ng template DNA. 2 U Vent polymerase (New England Biolabs) in 100 μl of supplied buffer were incubated 30 times under oil at 98° C. for one minute and 70° C. for five minutes (8). The DNA was extracted with chloroform/isoamyl alcohol, precipitated with ethanol and resuspended in TE-buffer (40). Sequence analysis was done according to the dideoxy-chain termination method (41) to confirm the accuracy of the PCR products.

Synthesis of oligonucleotides. Oligonucleotides were synthesized in a Gene Assembler Plus apparatus according to the manufacturers protocol (Pharmacia Biotech, Freiburg, Germany).

Results

Figure 4:
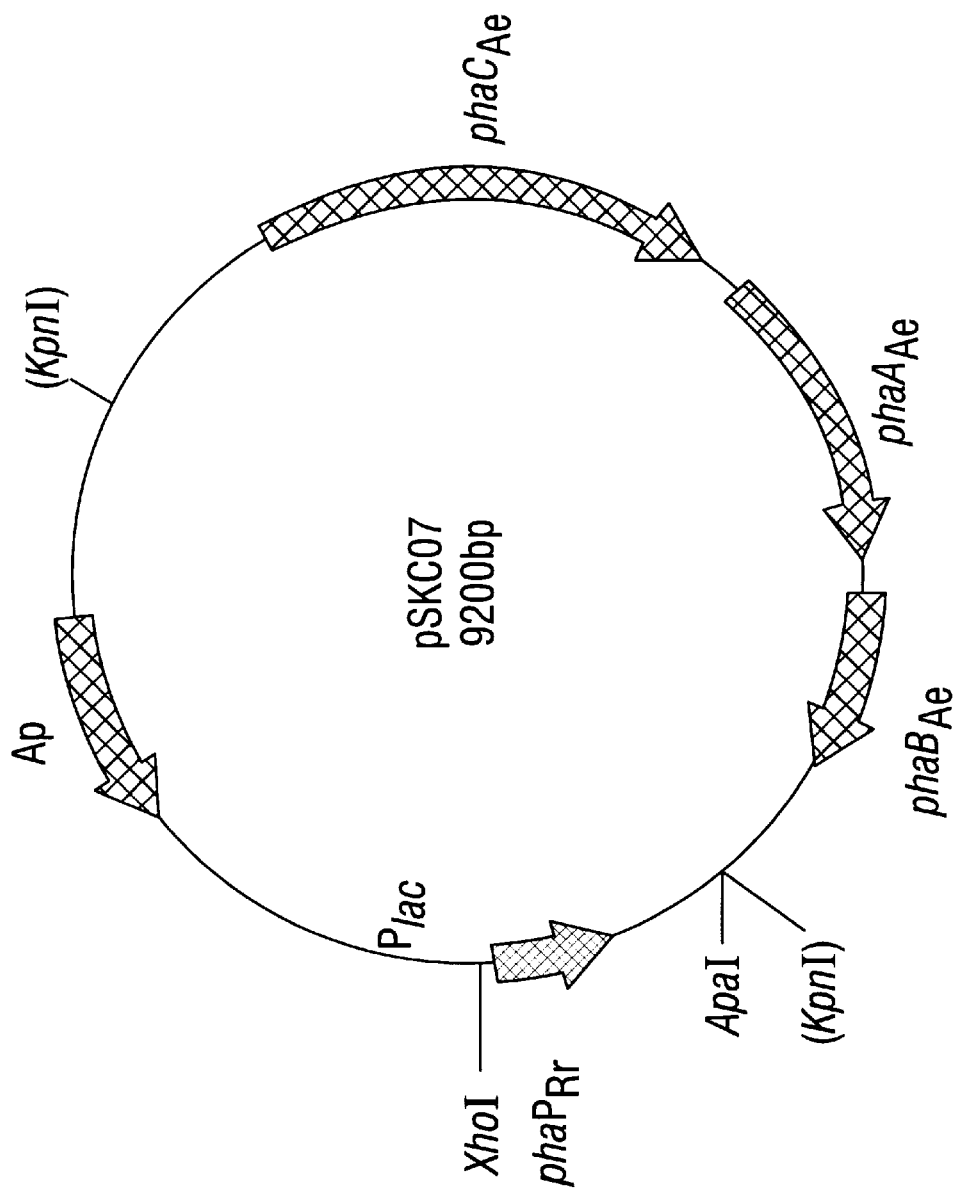
FIG. 4. Physical map of the hybride plasmid pSKCO7. The plasmid contained the structural gene of the GA14-protein of *R. ruber* (phaP$_{Rr}$) and the PHB-operon of *A. eutrophus* (phaCAB$_{Ae}$). The KpnI-restriction sites are shown in brackets because they were destroyed by the manipulations during the construction of the plasmid. Ap. ampicillin resistance gene, P$_{lac}$ lac-promoter.

Construction of the hybrid plasmid pSKC07 containing phaP$_{Rr}$ and phaCAB$_{Ae}$. In order to investigate the function of the PHA granule-associated GA14-protein or *R. ruber*, it was coexpressed with the PHB-operon of *A. eutrophus*. First, plasmid pSKXA10* that was previously constructed for the overexpression of the GA14-protein (36) was digested with KpnI, the restriction site of which is localized downstream of phaP$_{Rr}$ represents the structural gene of GA14-protein and was previously referred to as ORF3 (35, 36). Blunt ends were prepared by the exonuclease activity of the Klenow fragment of DNA polymerase I. Second, a 5.2-kbp SmaI-EcoRI-restriction fragment of plasmid pSK2665 (45) that contained the PHB-biosynthesis operon of *A. eutrophus* (phaCAB$_{Ae}$) was isolated and blunt ends were created by Mung bean nuclease. The ligation product of linearized pSKXA10* and of the 5.2-kbp-restriction fragment was referred to as pSKC07 and contained both phaP$_{Rr}$ and phaCAB$_{Ae}$ in antilinear orientation (FIG. 4). The PHB-operon includes the genes phaC$_{Ae}$, phaA$_{Ae}$ and phaB$_{Ae}$ encoding PHB synthase, 3-ketothiolase and NADPH-dependent acetoacetyl-CoA reductase, respectively. These genes are expressed from their own promoter (46), whereas the expression of phaP$_{Rr}$ is controlled by the lac-promoter (36).

Figure 5:
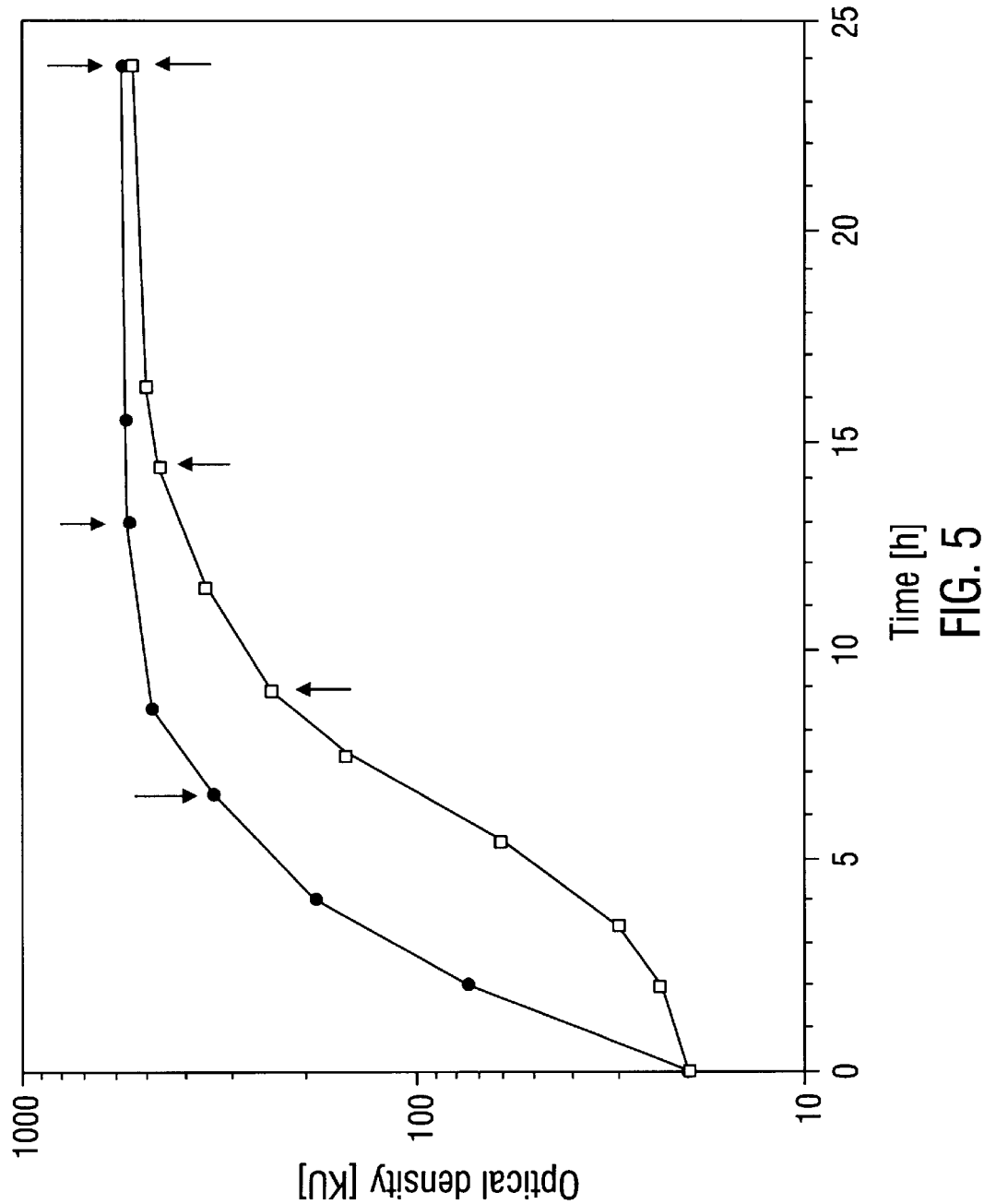
FIG. 5. Growth of *E. coli* XL1-Blue (pSKCO7) (square) and *E. coli* XL1-Blue (pSK2665) (●). Cells were cultivated at 37° C. in 300 ml LB medium with ampicillin, tetracycline and 1% (wt/vol) glucose. Aliquots of the cultures (50 ml) were collected at different times marked by arrow. KU, Klett units.

Investigation of the effect of GA14-protein on PHB biosynthesis in *E. coli*. The hybrid plasmids pSKC07 and PSK2665 were transformed into *E. coli* XLI-Blue, and cells of the recombinant strains were cultivated in LB complex medium. Growth of the cells was monitored by measuring the optical density of the cultures. Cells were collected at the end of the logarithmic and at the beginning as well as at the end of the stationary growth phase, and the PHB contents and the activities of the PHB-biosynthesis enzymes were measured. The expression of GA14-protein in *E. coli* XL1-Blue (pSKC07) over the period of growth was monitored by immuno dot blotting (data not shown). The growth rate of *E. coli* XL1-Blue (pSK2665) seemed to be higher than the growth rate of *E. coli* XL1-Blue (pSKCO7) (FIG. 5). However, accumulation of PHB in *E. coli* XL1-Blue (pSK2665) started already during the logarithmic growth phase whereas it started later in *E. coli* XL1-Blue (pSKCO7). Therefore, the stronger increase of the optical density during growth of *E. coli* XL1-Blue (pSK2665) could be due to the refraction of PHB granules. The maximal PHB content was more than 80% (wt/wt) of the cellular dry matter at the end of the stationary growth phase (Table 2) and was similar in both strains. Similarly, the activities of the PHB-biosynthesis enzymes were comparable in both strains and depended on the respective phase of PHB accumulation (Table 2). We therefore conclude that GA14-protein did not either positively or negatively affect the overall PHB accumulation in recombinant strains of *E. coli* except that it caused a short delay on the onset of PHB accumulation.

Formation of mini-granules by GA14-protein in *E. coli*. Interestingly, the PHB granules occurring in strain *E. coli* XL1-Blue (pSKCO7) were considerably smaller than those occurring in strain *E. coli* XL1-Blue (pSK2665). PHB granules were isolated from both strains, and the associated proteins were separated in SDS-polyacrylamide gels. Immunodetection using specific antibodies revelead that the GA14-protein is bound to PHB granules of strain *E. coli* XL1-Blue (pSKCO7). Postembedding immunogold labeling clearly demonstrated the localization of GA14-protein at the surface of the PHB granules as it was previously shown for this protein and for PHA granules isolated from cells of *R.* ruber (36). In *E. coli* XL1-Blue (pSK2665), which expressed only phaCAB$_{Ae}$, no GA14-protein was detectable.

Figure 6A:
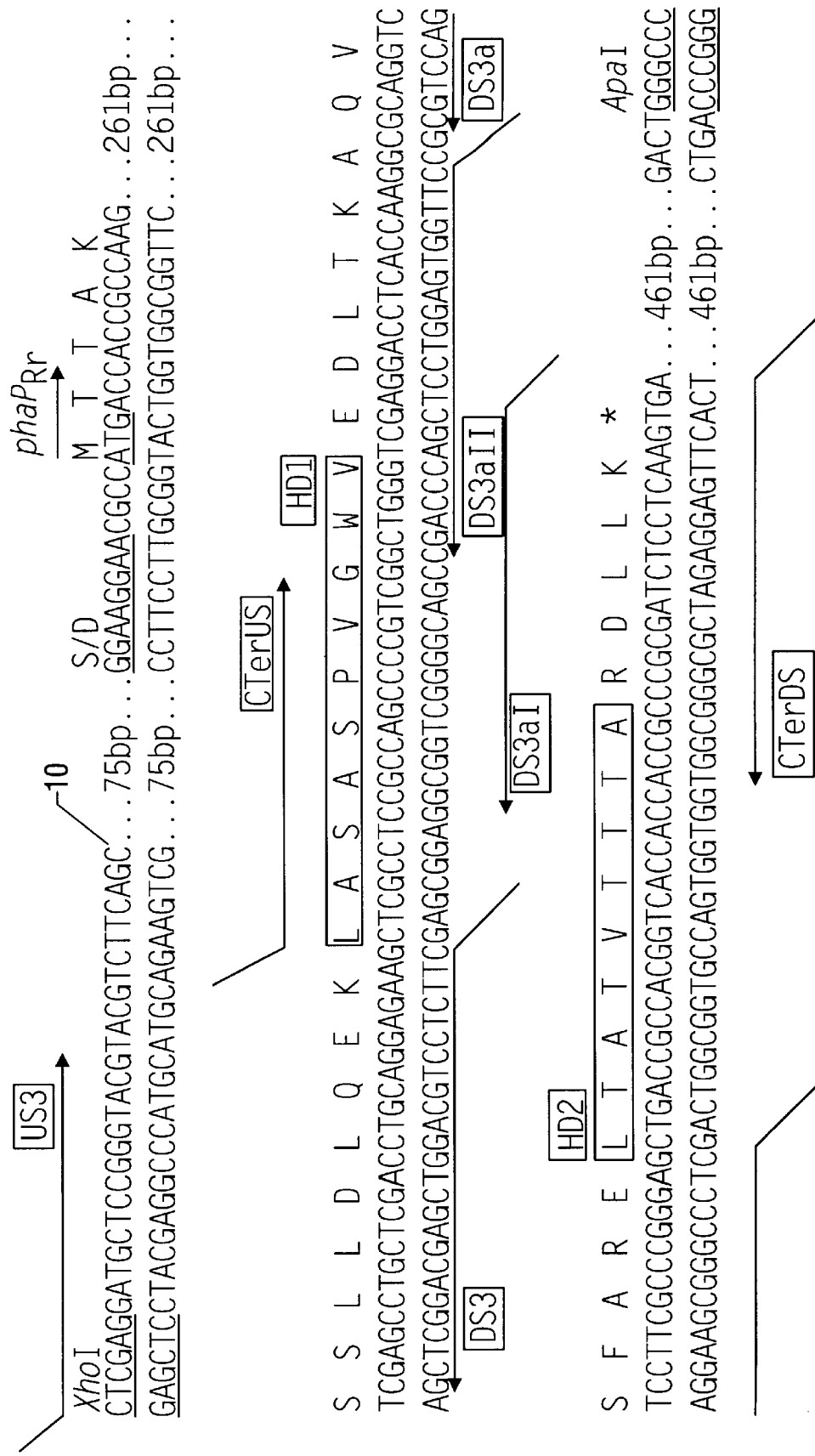
Figure 7A:
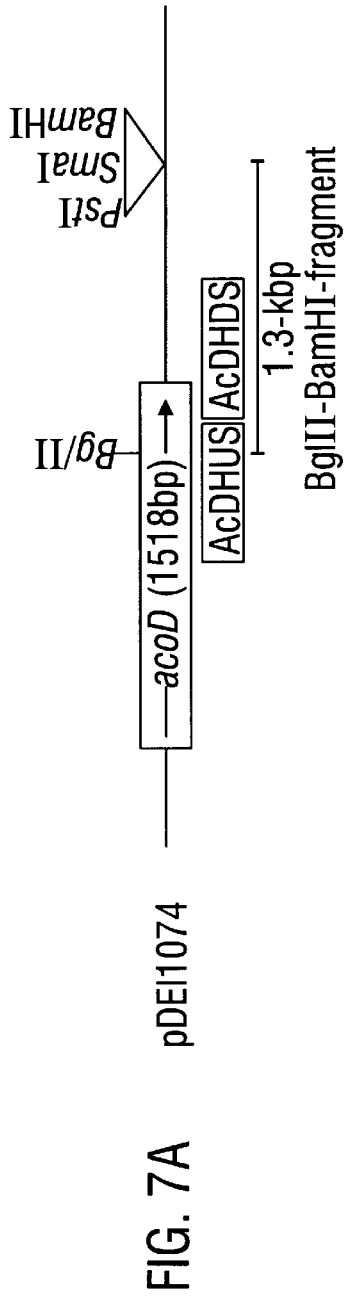
FIGS. 7A–7E. Construction of the fusion gene composed of acoD and of the C-terminal nucleotide sequence of phaP$_{Rr}$ and coexpression with the PHB-operon of *A. eutrophus*. Plasmid pBluescript KS⁻ DNA is shown by a thin line, genomic DNA of *A. eutrophus* is shown by a thick line, C, C-terminal nucleotide sequence of phaP$_{Rr}$. (a)–(d) Different hybride plasmids relevant for construction. (e) Nucleotide sequence of PCR-primers (SEQ ID NOS:23–24). Homologous parts to acoD are marked in capital letters, non-homologous parts to acoD are marked in small letters. Restriction sites are underlined.
Figure 7B:
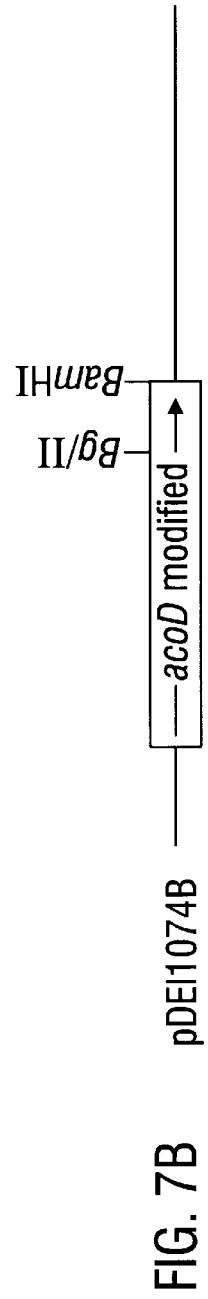
Figure 7C:
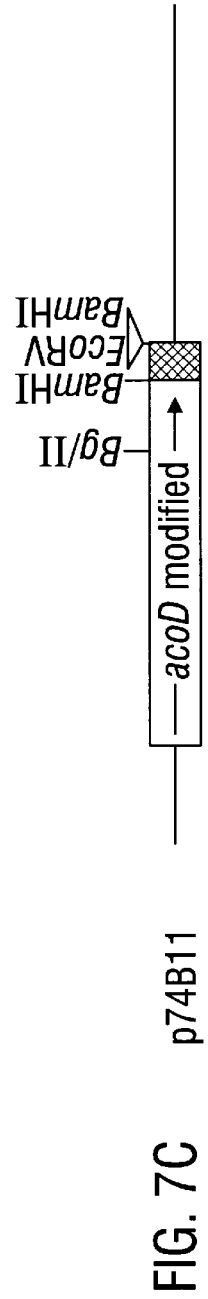
Figure 7D:
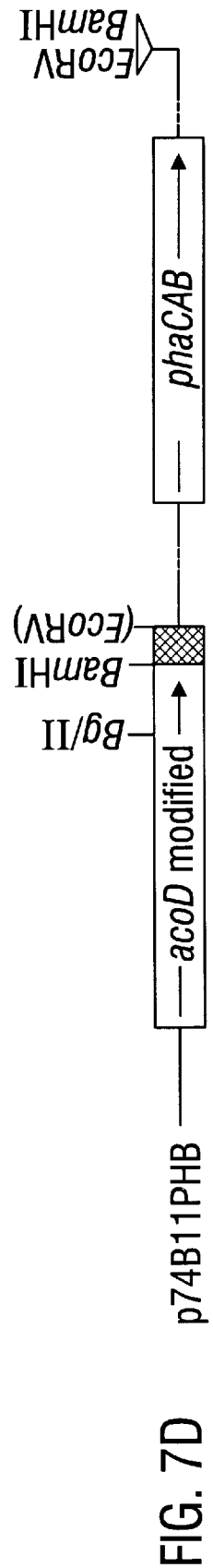
Figure 7E:

Construction of truncated variants of the GA14-protein. We postulated that the two C-terminal hydrophobic domains of the GA14-protein (HD1and HD2) mediate the association of this protein with a phospholipid monolayer that surrounds the core of the PHA granules in *R. ruber* (36). In order to proof this hypothesis, we constructed truncated variants of the GA14 protein, which were deleted for various parts of the C-terminal region, and investigated the ability of these modified forms to bind to the surface of granules in recombinant *E. coli* coexpressing the PHB-biosynthesis operon of *A. eutrophus*. DNA fragments encoding truncated variants of GA14-protein were synthesized by PCR (FIG. 6).

The PCR-primer US3 (FIG. 6) was homologous to the 5'-end of the 1.0-kbp XhoI-ApaI-fragment of plasmid pSKXA10* and, therefore, contained an XhoI-restriction site. Four different oligonucleotides (DS3, DS3aI, DS3aII, DS3a) (FIG. 6), which were homologous to different parts of the C-terminal nucleotide sequence of phaP$_{Rr}$, were used as second primers. These second primers contained, in addition to the matching bases, one stop codon as well as one ApaI-restriction site to allow the same cloning strategy that was used for the construction of the clones pSKXA10* and pSKCO7. The PCR-products were digested with XhoI and ApaI, and the generated XhoI-ApaI-fragments were ligated to pBluescript SK⁻ DNA that was treated with XhoI and ApaI; this yielded the hybrid plasmids pSKXA432, pSKXA462, pSKXA477 and pSKXA501, respectively.

The combination of the primers US3 and DS3 (FIG. 6) yielded the clone PSKXA432 that harbored a 432-bp XhoI-ApaI-fragment encoding a truncated GA14-protein without HD1 plus HD2 ($M_r$ 10,255, 101 amino acids). The 462-bp XhoI-ApaI-fragment of clone pSKXA462 encoded a truncated GA14-protein ($M_r$ 11,222, 111 amino acids) that stopped immediately downstream of HD1. The 477-bp XhoI-ApaI-fragment of pSKXA477 encoded a truncated GA14-protein ($M_r$ 11,808, 116 amino acids) containing HD1 plus five additional amino acids. This variant was constructed because we found a high similarity between the five amino acids downstream of HD1 (EDLTK; SEQ ID NO:26) or HD2 (RDLLK; SEQ ID NO:27) of wild type GA14-protein. Therefore, this sequence motif might be involved in the binding of the GA14-protein to the granules, or it might be required for the stability of the protein. Finally, the 501-bp XhoI-ApaI-fragment of pSKXA501 encoded a truncated GA14-protein ($M_r$ 12,697, 124 amino acids) that stopped immediately upstream of HD2.

Analysis of the PHB granule surface binding site of GA14-protein. The hybrid plasmids pSKXA432, pSKXA462, pSKXA477 and pSKXA501 were cut at their single KpnI-restriction sites, and blunt ends were created with the Klenow fragment of DNA polymerase I. Subsequently, the 5.2-kbp-fragment containing the PHB-biosynthesis operon of *A. eutrophus* was ligated to these linearized plasmids yielding pSKCO432, pSKCO462, pSKCO477 and pSKC0501, respectively. These plasmids contained the truncated variants of phaP$_{Rr}$ and phaCAB$_{Ae}$ in antilinear orientation. After transformation into *E. coli* XL1-Blue, the ability of the different truncated variants of the GA14-protein to bind to native PHB granules was investigated. Proteins of crude extracts, the soluble protein fraction after ultracentrifugaton and the granule-associated proteins of the different strains were separated in SDS-polyacrylamide gels and blotted onto nitrocellulose. The wild type GA14-protein as well as the different truncated variants of the GA14-protein were detected with polyclonal antibodies raised against the wild type GA14-protein. Wild type GA14-protein could be detected in crude extracts and in granule preparations of *E. coli* XL1-Blue (pSKC07), but it was absent from the soluble protein fraction. This indicated that in this strain the GA14-protein was completely bound to the PHB granules. The amount of other proteins, which were unspecifically bound to the granules, was not reduced. All truncated variants of the GA14-protein lacking HD1 or both HD1 plus HD2 were only detected in crude extracts and in the soluble protein fractions as revealed by the electropherograms and immunoblots obtained from cells of the strains *E. coli* XL1-Blue (pSKCO501), *E. coli* XL1-Blue (pSKCO477), *E. coli* XL1-Blue (pSKCO462) and *E. coli* XL1-Blue (pSKCO432), but they were not detected in the granule protein fraction. Therefore, those proteins have obviously lost the ability to bind to PHB granules.

Interestingly, the expression of the $M_r$ 12,697-, $M_r$ 11,808- and $M_r$ 11,222-variants of the GA14-protein, which lacked only HD2, was lower than the expression of the $M_r$ 10,255-variant, which lacked both HD1 plus HD2. Therefore, the antibody reaction with these proteins in the crude extract was very weak, and the bands corresponding to the truncated variants of the GA14-protein in the soluble protein fraction were rather faint. No signals were obtained with crude extracts or granule protein fractions prepared from cells of *E. coli* XL1-Blue (pSK2665) expressing the PHB-operon only. Some unspecific antibody reaction was observed with a higher $M_r$ protein of the crude extract and/or granule fraction of strain *E. coli* XL1-Blue (pSKCO7) and *E. coli* XL1-Blue (pSKCO462). The nature of this protein, however, is unknown.

Postembedding immunogold labeling of the strains *E. coli* XL1-Blue (pSKCO7) and *E. coli* XL1-Blue (pSKCO432) using GA14-specific polyclonal antibodies confirmed the results of the immunoblot analysis. Whereas in *E. coli* XL1-Blue (pSKCO7) the wild type GA14-protein was found only at the surface of the PHB granules, in *E. coli* XL1-Blue (pSKCO432) the truncated GA14-protein lacking both HD1 and HD2 was randomly distributed in the cytoplasm, but was not attached to the PHB granule surface. The incapability of binding to the granules significantly affected the size of the granules. In the recombinant strains *E. coli* XL1 Blue (pSKCO501), *E. coli* XL1-Blue (pSKCO477), *E. coli* XL1-Blue (pSKCO462) and *E. coli* XL1 Blue (pSKCO432) the granules were considerably larger than the granules in *E. coli* XL1-Blue (pSKCO7), which expressed the granule-associated wild type GA14-protein.

Construction of a fusion protein composed of AcDH-II and the C-terminus of the GA14-protein. A second approach was applied to confirm that the two C-terminal hydrophobic domains of the GA14-protein are responsible for the anchoring of the protein to the PHB granules. For this, we constructed a fusion gene that was composed of the gene acoD, which encoded the acetaldehyde dehydrogenase II (AcDH-II) of *A. eutrophus* (38), and of the C-terminal region of phaP$_{Rr}$. This construct was based on the pBluescript KS⁻ derivative pDel1074 that overproduced AcDH-II in *E. coli* XL1-Blue (37).

First, we eliminated the stop codon of acoD. For this, the 1.3-kbp BglII-BamHI-restriction fragment was removed from pDel1074 (FIG. 7). This fragment contained 314-bp of the 3'-region of acoD and approximately 1-kbp of genomic DNA of *A. eutrophus* located downstream of acoD. Using the primers AcDHUS and AcDHDS (FIG. 7) PCR was performed that produced a 320-bp fragment containing the 3'-region of acoD modified by the insertion of a BamHI-restriction site instead of the stop codon of acoD. This PCR product was ligated to the remaining BglII-BamHI-restriction fragment of pDel1074 that contained the 5'-region of acoD, yielding the plasmid pDel1074B (FIG. 7). In this construct the translation of acoD mRNA stopped 54 nucleotides downstream of acoD at the TAG stop codon in the T7 promoter region of pBluescript KS⁻. Second, a PCR-product was synthesized employing the oligonucleotides CterUS and CterDS as primers and plasmid PSKXA10* as template DNA (FIG. 6). The resulting 132-bp BamHI-fragment contained the 3'-terminal region of phaP$_{Rr}$ encoding the C-terminal region of the GA14-protein including HD1 and HD2, the stop codon downstream of phaP$_{Rr}$ and an additional EcoRV-restriction site. This BamHI-fragment was ligated into BamHI-digested pDel1074B yielding the plasmid p74B11 (FIG. 7). The blunt end restriction site for EcoRV in p74B11 was ligated to the 5.2-kbp fragment encoding the PHB-operon of A. eutrophus yielding the plasmid p74B11PHB (FIG. 7). In order to compare the ability of the modified AcDH-II protein to bind to PHB granules with that of the wild type AcDH-II protein, the 5.2-kbp fragment with the PHB-operon of A. eutrophus was also ligated to the blunt end SmaI-restriction site of pDel1074 (FIG. 7) yielding the plasmid pDel1074PHB. Both plasmids, p74B11PHB and pDel1074PHB, contained the modified or wild type acoD, respectively, and phaCAB$_{Ae}$ in colinear orientation.

Analysis of the ability of the modified AcDH-II to bind to the surface of PHB granules in vivo. The hybrid plasmids mentioned above were transformed into E. coli XL1 Blue, and the recombinant strains were cultivated in LB complex medium containing antibiotics, glucose and IPTG. The specific activity of AcDII-II was determined both in the soluble protein fraction and in the granule fraction (Table 3). The specific activity of the wild type AcDH-II was slightly higher (354 U/g) in E. coli XL1-Blue (pDel1074) that contained no PHB-operon, than in E. coli XL1-Blue (pDel1074PHB) that expressed the PHB-operon of A. eutrophus in addition (216 U/g). Modifications at the C terminus of AcDH-II resulted in a sharp decrease of the specific activity. E. coli XL1-Blue (pDel1074B) and E. coli XL1-Blue (p74B11) expressed only approximately 3% of AcDH II-activity (11 or 9 U/g, respectively). In E. coli XL1-Blue (p74B11PHB), which in addition expressed the PHB-operon, the activity was slightly higher (22 U/g). The activities of AcDH-II in the granule protein fractions of the strains E. coli XL1-Blue (pDel1074PHB) and E. coli XL1-Blue (p74B11PHB) were 3 and 5 U/g, respectively.

In further experiments the soluble proteins and the proteins of the granule preparations were separated in SDS-polyacrylamide gels and transferred onto nitrocellulose. Wild type and modified AcDH-II were detected with polyclonal antibodies raised against the wild type protein. In the soluble fraction of E. coli XL1-Blue (pDel1074) and E. coli XL1-Blue (pDel1074PHB) a strong band was visible in the electropherogram corresponding to the wild type AcDH-II exhibiting an M$_r$ of 54,819 (38); the occurrence of AcDH-II was confirmed by immunoblot analysis (FIG. 5; 38). An overproduction of modified AcDH-II containing the C-terminus of GA14-protein (M$_r$ 58,908) in E. coli XL1-Blue (p74B11) and E. coli XL1-Blue (p74B11PHB) was not observed, but the antibody reaction detected a protein with a slightly higher electrophoretic mobility as compared to wild type AcDH-II. In PHB granule preparations of E. coli XL1-Blue (pDel1074PHB) only a relatively small amount of wild type AcDH-II protein was observed, whereas in the electropherograms as well as in the immunoblots of the granule proteins of E. coli XL1-Blue (p74B11PHB) high amounts of the modified AcDH-II protein were detected. Therefore, we conclude that the C-terminus of GA14-protein of R. ruber mediated a much higher affinity of the modified AcDH-II to PHB granules in recombinant E. coli. The detection of low amounts of wild type AcDH-II at the PHB granules (FIG. 5) is probably due to a tendency of the protein to bind weakly but unspecifically to PHB granules. This was not astonishing in view of the tendency of PHB granules to adsorb various proteins of the cytoplasm of recombinant E. coli and in view of the strong overproduction of AcDH-II in E. coli XL1-Blue (pDel1074PHB).

In vitro binding of the modified AcDH-II to artificial PHB granules. Furthermore, the affinity of wild type and modified AcDH-II to artificial PHB granules that contained no phospholipid monolayer was investigated. For this, crude extract proteins of the strains E. coli XL1-Blue (pDel1074) and E. coli XL1-Blue (p74B11) were incubated with artificial PHB granules. Subsequently, the granules were washed, and associated proteins were analysed by SDS-polyacrylamide gel electrophoresis and immunoblotting using AcDH-II-specific antibodies. It was clearly demonstrated that the modified AcDH-II proteins efficiently bound to the artificial granules, whereas the wild type AcDH-II protein was only visible as a faint band among several other proteins, which were adsorbed unspecifically to the granules.

The native GA14-protein, which was purified from E. coli XL1-Blue (pSKXA10*), was also able to associate to artificial PHB granules (data not shown).

Discussion

The function of the PHA granule associated GA14-protein from R. ruber was investigated in E. coli following coexpression with the PHB-biosynthesis operon of A. eutrophus. This strategy was necessary because of the genetic inaccessibility of R. ruber wild type and mutants defective in PHA biosynthesis (36) and because of the inability of recombinant E. coli to accumulate PHA after transformation with the PHA synthase gene locus of R. ruber (35). Coexpression of the GA14-protein (phaP$_{Rr}$) plus the PHB-biosynthesis pathway (phaCAB$_{Ac}$) in E. coli XL1-Blue (pSKCO7) did not increase the amount of accumulated PHB or the activities of the biosynthesis enzymes as compared to E. coli XL1-Blue (pSK2665), which only expressed the PHB-biosynthesis pathway. The only but interesting effect of the coexpression of phaP$_{Rr}$ and phaCAB$_{Ae}$ was the formation of mini-granules in E. coli XL1-Blue (pSKCO7) due to the association of the GA14-protein to the PHB granule surface as demonstrated by immunoelectron microscopy. A decoration of the GA14-protein at the cell membrane as described for R. ruber wild type or E. coli XL1-Blue (pSKXA10*) (36) was not observed in E. coli XL1-Blue (pSKCO7). One explanation could be that the amount of GA14-protein in the cells of E. coli XL1-Blue (pSKCO7) was lower than in the strains mentioned above, and that, in addition, the GA14-protein has a higher affinity to the granules than to the cell membrane. The formation of mini-granules has already been observed in A. eutrophus. Mutants defective in the gene phaP$_{Ae}$ encoding the granule-associated GA24-protein contained only one big PHB granule. However, subsequent to the complementation of this mutant with a hybrid-plasmid harboring phaP$_{Ae}$, a large number of rather small granules were detected (57). Interestingly, there are also similarities to oil bodies of plants. Small oil bodies of pollen or seeds are surrounded by proteins that are referred to as oleosins and are attached to the phospholipid monolayer on the surface of these oil bodies. Big oil bodies of fruits, on the other hand, lack these oleosins (30). These similarities of the GA14- protein of *R. ruber* and the GA24-protein of *A. eutrophus* to the oleosins of plants prompted us to refer to these PHA granule-associated proteins as phasins (51). The analysis of PHB accumulating cells of *E. coli* expressing truncated forms of the GA14-protein clearly demonstrated that the loss of only HD2 impaired the modified GA14-protein to bind to the surface of PHB granules.

The analysis of PHB accumulating cells of *E. coli* expressing the fusion protein consisting of AcDH-II plus the C-terminus of the GA14-protein, and studies of this fusion protein regarding its binding to artificial PHB granules demonstrated that the fusion protein was bound very efficiently to native or artificial granules. AcDH-II was not the most suitable protein because the experiments clearly revealed that modifications at the C-terminus, i.e., the removal of the stop codon and extension of the enzyme by 18 amino acids in clone pDel1074B, reduced the specific activity drastically. Therefore, the PHB granule-bound enzyme was mostly inactive. In principle, however, these experiments revealed the possibility to immobilize any suitable protein at a PHB matrix. This might be of biotechnological interest since PHB or other PHA are a rather cheap material for this purpose and since these polyesters are accessible to biodegradation under mild conditions.

Previous results had suggested that the hydrophobic domains HD1 and HD2 at the C-terminus of the GA14-protein might be responsible for anchoring of this protein in a phospholipid monolayer surrounding the PHA granule core in *R. ruber* (36). Now, the results obtained in this study confirmed this hypothesis due to (I) the inability of the different truncated variants of the GA14-protein lacking HD2 or both HD1 plus HD2 to bind to PHB granules, and due to (ii) the binding of the modified AcDH-II containing the C-terminus of the GA14-protein to native PHB granules. The association of modified AcDH-II and wild type GA14-protein to artificial PHB granules implies that HD1 and/or HD2 could also directly interact with the PHA granule surface even without the involvement of a phospholipid monolayer. In this context, HD2, which is a stretch of nine amphiphilic or hydrophobic amino acids, is of special interest since five of the nine amino acids are threonines. Similar threonine-rich sequences were also observed at the C-terminus of extracellular PHB depolymerases of *Pseudomonas lemoignei*, and they were considered as the substrate-binding domain of these depolymerases (4, 17).

References

1. Anderson, A. J., and E. A. Dawes. 1990. Occurrence, metabolism, metabolic role, and industrial uses of bacterial polyhydroxyalkanoates. Microbiol. Rev. 54: 450–472.
2. Bradford, M. M. 1976. A rapid and sensitive method for the quantitation of microgram quantities of protein utilizing the principle of protein-dye binding. Anal. Biochem. 72: 248–254.
3. Brandl, H., R. A. Gross, R. W. Lenz, and R. C. Fuller. 1988. *Pseudomonas oleovarans* as a source of poly(β-hydroxyalkanoates) for potential applications as biodegradable polyesters. Appl. Environ. Microbiol. 54: 1977–1982.
4. Briese, B. H., B. Schmidt, and D. Jendrossek. 1994. *Pseudomonas lemoignei* has five poly(hydroxyalkanoic acid) (PHA) depolymerase genes: a comparative study of bacterial and eukaryotic PHA depolymerases. J. Environ. Polym. Degrad. 2: 75–87.
5. Bullock, W. O., J. M. Fernandez, and J. M. Short. 1987. XL-1-Blue: a high efficiency plasmid transforming recA *Escherichia coli* strain with beta-galactosidase selection. BioTechniques 5: 376–379.
6. Devereux, J., P. Haeberli, and O. Smithies. 1984. A comprehensive set of sequence analysis programs for the VAX. Nucleic Acids Res. 12: 387–395.
7. Duchamel, R. C., and D. A. Johnson. 1985. Use of nonfat dry milk to block nonspecific nuclear and membrane staining by avidin conjugates. J. Histochem. Cytochem. 33: 711–714.
8. Dutton, C. M., C. Paynton, and S. S. Sommer. 1993. General method for amplifying regions of very high G+C content. Nucleic Acids Res. 21: 2953–2954.
9. Ellar, D. and D. G. Lundgren. 1968. Morphology of poly-β-hydroxybutyrate granules. J. Mol. Biol. 35: 489–502.
10. Gerngross, T. U., P. Reilly, J. Stubbe, A. J. Sinskey, and O. P. Peoples. Immunocytochemical analysis of poly-β-hydroxybutyrate (PHB) synthase in *Alcaligenes eutrophus* H16:localization of the synthase enzyme at the surface of PHB granules. J. Bacteriol. 175: 5289–5293.
11. Griebel, R., Z. Smith, and J. M. Merrick. 1968. Metabolism of poly-β-hydroxybutyrate. I. Purification, composition, and properties of native poly-β-hydroxybutyrate granules from *Bacillus megaterium*. Biochemistry 7: 3676–3681.
12. Hanahan, D. 1985. Techniques for transformation of *E. coli*. P. 109–135. In D. M. Glover (ed.), DNA cloning, a practical approach. IRL Press, Oxford, Washington, D.C.
13. Haywood, G. W., A. J. Anderson, D. R. Williams, E. A. Dawes, and D. F. Ewing. 1991. Accumulation of a poly (hydroxyalkanoate) copolymer containing primarily 3-hydroxy-valerate from simple carbohydrate substrates by Rhodococcus sp. NCIMB 40126. Int. J. Biol. Macromol. 13: 83–88.
14. Haywood, G. W., A. J. Anderson, L. Chu, and E. A. Dawes. 1988. The role of NADH- and NADPH-linked acetoacetyl-CoA reductases in the poly-3-hydroxybutyrate synthesizing organism *Alcaligenes eutrophus*. FEMS Microbiol. Lett. 52: 529–264.
15. Holmes, P. A. 1985. Applications of PHB—a microbially produced biodegradable thermoplastic. Phys. Technol. 16: 32–36.
16. Huang, A. H. C. 1992. Oil bodies and oleosins in seeds. Annu. Rev. Plant Physiol. Plant Mol. Biol. 43: 177–200.
17. Jendrossek, D., A. Frisse, A. Behrends, M. Andermann, H. D. Kratzin, T. Stanislawski, and H. G. Schlegel. 1995. Biochemical and molecular characterization of the *Pseudomonas lemoignei* polyhydroxyalkanoate depolymerase system. J. Bacteriol. in press.
18. Jendrossek, D., A. Steinbüchel, and H. G. Schlegel, 1987. Three different proteins exhibiting NAD-dependent acetaldehyde dehydrogenase activity from *Alcaligenes eutrophus*. Eur. J. Biochem. 167: 541–548.
19. Jendrossek. D., I. Knoke, R. B. Habibian, A. Steinbüchel, and H. G. Schlegel. 1993. Degradation of poly(3-hydroxybutyrate), PHB, by bacteria and purification of a novel PHB depolymerase from Comamonas sp. J. Environ. Polym. Degrad. 1: 53–63.
20. Kaudewitz, F. 1959. Inaktivienende and mutagene Wirkung salpetriger Säure auf Zellen von *Escherichia coli*. Z. Naturforschg. 14b: 528–537.
21. Konigsberg, W. H., and L. Henderson. 1983. Removal of sodium dodecyl sulfate from proteins by ion-pair extraction. Meth. Enzymol. 91: 254–259.
22. Koning, G. J. M., and I. A. Maxwell. 1993. Biosynthesis of poly-(R)-3-hydroxyalkanoate: an emulsion polymerization. J. Environ. Polym. Degrad. 1: 223–226.
23. Kyte, J., and R. F. Doolittle. 1982. A simple method for displaying the hydropathic character of a protein. J. Mol. Biol. 157: 105–132.

24. Laemmli, U. K. 1970. Cleavage of structural proteins during the assembly of the head of bacteriophage T4. Nature 227: 680–685.
25. Liebergesell, M., B. Schmidt, and A. Steinbüchel. 1992. Isolation and identification of granule-associated proteins relevant for poly(3-hydroxyalkanoic acid) biosynthesis is *Chromatium vinosum* D. FEMS Microbiol. Lett. 99: 227–232.
26. Liebergesell, M., K. Sonomoto, M. Madkour, F. Mayer, and A. Steinbüchel. 1994. Purification and characterization of the poly(hydroxyalkanoic acid) synthase from *Chromatium vinosum* and localization of the enzyme at the surface of poly(hydroxyalkanoic acid) granules. Eur. J. Biochem. 226: 71–80.
27. Lundgren, D. G., R. M. Pfister, and J. M. Merrick, 1964. Structure of poly-β-hydroxybutyric acid granules. J. Gen. Microbiol. 34: 441–446.
28. Mayer, F. 1992. Structural aspects of poly-β-hydroxybutyrate granules. FEMS Microbiol. Rev. 103: 265–267.
29. Mayer, F., J. C. Wallace, and D. B. Keech. 1980. Further electron microscope studies on pyruvate carboxylase. Eur. J. Biochem. 112: 265–272.
30. Murphy, D. J. 1993. Structure, function and biogenesis of storage lipid bodies and oleosins in plants. Prog. Lipid Res. 32: 247–280.
31. Nishimura, T., T. Saito, and K. Tomita. 1978. Purification and properties of β-ketothiolase from *Zoogloea ramigera*. Arch. Microbiol. 116: 21–27.
32. Olmsted, J. B. 1981. Affinity purification of antibodies from diazotized paper blots of heterogeneous protein samples. J. Biol. Chem. 256: 11955–11957.
33. Pedros-Alio, C., J. Mas, and R. Guerrero. 1985. The influence of poly-β-hydroxybutyrate accumulation on cell volume and buoyant density in *Alcaligenes eutrophus*. Arch. Microbiol. 143: 178–184.
34. Peoples, O. P., and A. J. Sinskey. 1989. Poly-β-hydroxybutyrate (PHB) biosynthesis in *Alcaligenes eutrophus* H16. Identification and characterization of the PHB polymerase gene (phbC). J. Biol. Chem. 264: 15298–15303.
35. Pieper, U., and A. Steinbüchel. 1992. Identification, cloning and sequence analysis of the poly(3-hydroxyalkanoic acid) synthase gene of the Gram-positive bacterium *Rhodococcus ruber*. FEMS Microbiol. Lett. 96: 73–80.
36. Pieper-Fürst, U., M. H. Madkour, F. Mayer, and A. Steinbüchel. 1994. Purification and characterization of a 14-kilodalton protein that is bound to the surface of polyhydroxyalkanoic acid granules in *Rhodococcus ruber*. J. Bacteriol. 176: 4328–4337.
37. Priefert, H., and A. Steinbüchel. 1993. Overproduction of a stable acetaldehyde dehydrogenase with high affinity to acetaldehyde by *Escherichia coli* expressing the acoD gene of *Alcaligenes eutrophus*. Biotechnol. Lett. 15: 443–448.
38. Priefert, H., N. Krüger, D. Jendrossek, B. Schmidt, and A. Steinbüchel. 1992. Identification and molecular characterization of the gene coding for acetaldehyde dehydrogenase II (acoD) of *Alcaligenes eutrophus*. J. Bacteriol. 174: 899–907.
39. Roth, J., M. Bendayan, E. Carlemalm, W. Villinger, and M. Garavito. 1981. Enhancement of structural preservation and immunocytochemical staining in low temperature embedded pancreatic tissue. J. Histochem. Cytochem. 29: 663–669.
40. Sambrook, J., E. F. Fritsch, and T. Maniatis. 1989. Molecular cloning: a laboratory manual, $2^{nd}$ ed. Cold Spring Harbor Laboratory, Cold Spring Harbor, N.Y.
41. Sanger, F., S. Nicklen, and A. R. Coulson. 1977. DNA sequencing with chain-terminating inhibitors. Proc. Natl. Acad. Sci. USA 74: 5463–5467.
42. Schlegel, H. G., R. Lafferty, and I. Krauss, 1970. The isolation of mutants not accumulating poly-β-hydroxybutyric acid. Arch. Mikrobiol. 71: 283–294.
43. Schlegel, H. G., H. Kaltwasser, and G. Gottschalk. 1961. Bin Submersverfahren zur Kultur wasserstoffoxidierender Bakterien: Wachstumsphysiologische Untersuchumgen. Arch. Mikrobiol. 38: 209–222.
44. Schubert, P., A. Steinbüchel, and H. G. Schlegel. 1988. Cloning of the *Alcaligenes eutrophus* genes for synthesis of poly-β-hydroxybutyric acid (PHB) and synthesis of PHB in *Escherichia coli*. J. Bacteriol. 170: 5837–5847.
45. Schubert, P., A. Steinbüchel, and H. G. Schlegel. 1989. Genes involved in the synthesis of poly(β-hydroxyalkanoic acid) in *Alcaligenes eutrophus*, p. 433–436. In D. Behrens and A. J. Driesel (ed.), DECHEMA Biotechnology Conferences, vol. 3, part A, VCH Wainheim, Federal Republic of Germany.
46. Schubert, P., N. Krüger, and A. Steinbüchel. 1991. Molecular analysis of the *Alcaligenes eutrophus* poly(3-hydroxybutyrate) biosynthetic operon: identification of the N-terminus of poly(3-hydroxybutyrate) synthase and identification of the promoter. J. Bacteriol. 173: 168–175.
47. Slater, S. C., W. H. Voige, and D. F. Dennis. 1988. Cloning and expression in *Escherichia coli* of the *Alcaligenes eutrophus* H16 poly-β-hydroxybutyrate biosynthetic pathway. J. Bacteriol. 170: 4431–4436.
48. Steinbüchel, A. 1991. Polyhydroxyalkanoic acids, p. 123–213. In D. Byrom (ed.), Biomaterials, Novel Materials from Biological Sources. Macmillan Publishers Ltd., Basingstoke.
49. Steinbüchel, A., and H. G. Schlegel. 1991. Physiology and molecular genetics of poly(β-hydroxyalkanoic acid) synthesis in *Alcaligenes eutrophus*. Mol. Microbiol. 5: 535–542.
50. Steinbüchel, A., E. Hustede, M. Liebergesell, U. Pieper, A. Timm, and H. Valentin. 1992. Molecular basis for biosynthesis and accumulation of polyhydroxyalkanoic acids in bacteria. FEMS Microbiol. Rev. 103: 217–230.
51. Steinbüchel, A., K. Aerts, W. Babel, C. Föllner, M. Liebergesell, M. H. Madkour, F. Mayer, U. Pieper-Fürst, A. Pries, H E. Valentin, and R. Wieczorek. Considerations on the structure and biochemistry of bacterial polyhydroxyalkanoic acid granules and introducing the terms GAP and phasin. Lecture presented at the international symposium on bacterial polyhydroxyalkanoates (ISBP 94) in Montreal, Aug. 15, 1994.
52. Timm, A., and A. Steinbüchel. 1990. Formation of polyesters consisting of medium-chain-length 3-hydroxyalkanoic acids from gluconate by *Pseudomonas aeruginosa* and other fluorescent pseudomonals. Appl. Environ. Microbiol. 56: 3360–3367.
53. Valentin, H. E., and A. Steinbüchel. 1994. Application of enzymatically synthesized short-chain-length hydroxy fatty acid coenzyme A thioesters for assay of polyhydroxyalkanoic acid synthases. Appl. Microbiol. Biotechnol. 40: 699–709.
54. Valentine, R. C., B. M. Shapiro, and E. R. Stadtman. 1968. Regulation of glutamine synthetase. XII. Electron microscopy of the enzyme from *Escherichia coli*. Biochemistry 7: 2143–2152.
55. Vogelstein, B., and D. Gillespie. 1979. Preparative and analytical purification of DNA from agarose. Proc. Natl. Acad. Sci. U.S.A. 76: 615–619.

56. Weber, K., and M. Osborn. 1969. The reliability of molecular weight determinations by dodecyl sulfate polyacrylamide gel electrophoresis. J. Biol. Chem. 244: 4406–4412.
57. Wieczorek, R., A. Pries, A. Steinbüchel, and F. Mayer. Unpublished data.

TABLE 1

Bacterial strain and plasmids used in this study

| Strain or plasmid | Relevant characteristics | Source or reference |
| --- | --- | --- |
| Strain |  |  |
| *Escherichia coli* |  |  |
| XL1-Blue | recA1 endA1 gyrA96 thi1 hsdr17 ($r_K^-$ $m_K^+$) supE44 relA1 λ⁻ luc⁻ [P proAB lacI$^q$ZΔM15 TnIO(tet)] | 5 |
| Plasmids |  |  |
| pBluescript SK⁻ | Ap$^r$ lacPOZ' | Stratagene |
| pBluescript KS | Ap$^r$ lacPOZ' | Stratagene |
| pSK2665 | harboring the PHB-operon of *Alcaligenes eutrophus* | 27 |
| pSKXA10* | harboring wild type phaP$_{Kr}$ (414 bp) | 21 |
| pSKXA501 | harboring truncated phaP$_{Kr}$ (372 bp) | this study |
| pSKXA477 | harboring truncated phaP$_{Rr}$ (348 bp) | this study |
| pSKXA462 | harboring truncated phaP$_{Rr}$ (333 bp) | this study |
| pSKXA432 | harboring truncated phaP$_{Rr}$ (303 bp) | this study |
| pSKCO7 | corresponds to pSKXA10*, but contains in addition the PHB-operon of *A. eutrophus* | this study |
| pSKCO501 | corresponds to pSKXA501, but contains in addition the PHB-operon of *A. eutrophus* | this study |
| pSKCO477 | corresponds to pSKXA477, but contains in addition the PHB-operon of *A. eutrophus* | this study |
| pSKCO462 | corresponds to pSKXA462, but contains in addition the PHB-operon of *A. eutrophus* | this study |
| pSKCO432 | corresponds to pSKXA432, but contains in addition the PHB-operon of *A. eutrophus* | this study |
| pDel1074 | harboring acoD of *A. eutrophus* | 23 |
| pDel1074PHB | corresponds to pDel1074, but contains in addition the PHB-operon of *A. eutrophus* | this study |
| pDel1074B | harboring modified acoD | this study |
| p74B11 | harboring a fusion gene of modified acoD and the C-terminus of GA14-protein of *Rhodococcus ruber* | this study |
| p74B11PHB | corresponds to p74B11, but contains in addition the PHB-operon of *A. eutrophus* | this study |

TABLE 2

PHB content and specific activities of PHB-biosynthetic enzymes during growth of *E. coli* XL1-Blue (pSKCO7) and *E. coli* XL1-Blue (pSK2665)

|  |  |  | Specific activities of |  |  |
| --- | --- | --- | --- | --- | --- |
| Strain | Time [h] | PHB [%, wt/wt] | PHB synthese [U/g protein] | 3-Ketothiolase [U/mg protein] | NADPH-dependent acetoacetyl-CoA reductase [U/g protein] |
| *E. coli* | 9 | 8 | 14 | 2.8 | 11 |
| XL1-Blue | 14.5 | 57 | 66 | 10.9 | 44 |
| (pSKCO7) | 24 | 81 | 19 | 6.2 | 27 |
| *E. coli* | 6.5 | 34 | 60 | 6.0 | 16 |
| XL1-Blue | 13 | 61 | <10 | 11.4 | 28 |
| (pSK2665) | 24 | 85 | <10 | 3.2 | 13 |

TABLE 3

Specific activities of wild type AcDH-II and modified AcDH II containing the C-terminus of GA14-protein

| Sample[a] | Specific activity of AcDH-II [U/g] |
| --- | --- |
| Soluble protein fraction of *E. coli* |  |
| XL1-Blue (pDel1074) | 354 |
| XL1-Blue (pDel1074PHB) | 216 |
| XL1-Blue (pDel1074B) | 11 |
| XL1-Blue (p74B11) | 9 |
| XL1-Blue (p74B11PHB) | 22 |
| XL1-Blue (pSK2665) | 0 |
| PHB granule protein fraction of *E. coli* |  |
| XL1-Blue (pDel1074PHB) | 3 |
| XL1-Blue (p74B11PHB) | 5 |

[a]Protein fractions were prepared following a 24 h-incubation at 37° C. in 50 ml LB-medium with ampicillin, tetracycline, 0.1 mM IPTG and 0.2% (wt/vol) glucose.

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
      (A) LENGTH: 12 base pairs
      (B) TYPE: nucleic acid
      (C) STRANDEDNESS: single
      (D) TOPOLOGY: unknown (xi) SEQUENCE DESCRIPTION: SEQ ID NO: 1:

TCGACCTCGA GG                                   12

(2) INFORMATION FOR SEQ ID NO: 2:

(i) SEQUENCE CHARACTERISTICS:
        (A) LENGTH: 80 base pairs
        (B) TYPE: nucleic acid
        (C) STRANDEDNESS: single
        (D) TOPOLOGY: unknown (xi) SEQUENCE DESCRIPTION: SEQ ID NO: 2:

ACGGAAGGAA CGCCATGACC ACCGCCAAGA CCCCGGTCGA CGCCGCCGTC GCCAAGACCA    60

CCGCCGACGC CGCCAAGGCC    80

(2) INFORMATION FOR SEQ ID NO: 3:

(i) SEQUENCE CHARACTERISTICS:
        (A) LENGTH: 12 base pairs
        (B) TYPE: nucleic acid
        (C) STRANDEDNESS: single
        (D) TOPOLOGY: unknown (xi) SEQUENCE DESCRIPTION: SEQ ID NO: 3:

CTCCTCAAGT GA    12

(2) INFORMATION FOR SEQ ID NO: 4:

(i) SEQUENCE CHARACTERISTICS:
        (A) LENGTH: 19 base pairs
        (B) TYPE: nucleic acid
        (C) STRANDEDNESS: single
        (D) TOPOLOGY: both (xi) SEQUENCE DESCRIPTION: SEQ ID NO: 4:

CTGGACTGGG CCCGGTACC    19

(2) INFORMATION FOR SEQ ID NO: 5:

(i) SEQUENCE CHARACTERISTICS:
        (A) LENGTH: 4 amino acids
        (B) TYPE: amino acid
        (C) STRANDEDNESS: unknown
        (D) TOPOLOGY: unknown (xi) SEQUENCE DESCRIPTION: SEQ ID NO: 5:

Ser Thr Ser Arg
1

(2) INFORMATION FOR SEQ ID NO: 6:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (xi) SEQUENCE DESCRIPTION: SEQ ID NO: 6:

Thr Glu Gly Thr Pro
1               5

(2) INFORMATION FOR SEQ ID NO: 7:

(i) SEQUENCE CHARACTERISTICS:
        (A) LENGTH: 22 amino acids
        (B) TYPE: amino acid
        (C) STRANDEDNESS: unknown
        (D) TOPOLOGY: unknown (xi) SEQUENCE DESCRIPTION: SEQ ID NO: 7:

Met Thr Thr Ala Lys Thr Pro Val Asp Ala Ala Val Ala Lys Thr Thr
    1               5                   10                  15

Ala Asp Ala Ala Lys Ala
                20

(2) INFORMATION FOR SEQ ID NO: 8:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (xi) SEQUENCE DESCRIPTION: SEQ ID NO: 8:

Xaa Xaa Ala Lys Thr Pro Val Asp Ala Ala Val Ala Lys Thr Thr Ala
    1               5                   10                  15

Asp Ala Ala Lys
                20

(2) INFORMATION FOR SEQ ID NO: 9:

(i) SEQUENCE CHARACTERISTICS:
        (A) LENGTH: 46 amino acids
        (B) TYPE: amino acid
        (C) STRANDEDNESS: unknown
        (D) TOPOLOGY: unknown (xi) SEQUENCE DESCRIPTION: SEQ ID NO: 9:

Ser Ser Leu Leu Asp Leu Gln Glu Lys Leu Ala Ser Ala Ser Pro Val
    1               5                   10                  15

Gly Trp Val Glu Asp Leu Thr Lys Ala Gln Val Ser Phe Ala Arg Glu
                20                  25                  30

Leu Thr Ala Thr Val Thr Thr Thr Ala Arg Asp Leu Leu Lys
                35                  40                  45

(2) INFORMATION FOR SEQ ID NO: 10:

(i) SEQUENCE CHARACTERISTICS:
        (A) LENGTH: 33 base pairs
        (B) TYPE: nucleic acid
        (C) STRANDEDNESS: double
        (D) TOPOLOGY: unknown (xi) SEQUENCE DESCRIPTION: SEQ ID NO: 10:

CTCGAGGATG CTCCGGGTAC GTACGTCTTC AGC                                          33

(2) INFORMATION FOR SEQ ID NO: 11:

(i) SEQUENCE CHARACTERISTICS:
        (A) LENGTH: 27 base pairs
        (B) TYPE: nucleic acid
        (C) STRANDEDNESS: double
        (D) TOPOLOGY: unknown (xi) SEQUENCE DESCRIPTION: SEQ ID NO: 11:

GGAAGGAACG CCATGACCAC CGCCAAG                                                 27

(2) INFORMATION FOR SEQ ID NO: 12:

(i) SEQUENCE CHARACTERISTICS:
        (A) LENGTH: 141 base pairs
        (B) TYPE: nucleic acid
        (C) STRANDEDNESS: double
        (D) TOPOLOGY: unknown (xi) SEQUENCE DESCRIPTION: SEQ ID NO: 12:

TCGAGCCTGC TCGACCTGCA GGAGAAGCTC GCCTCCGCCA GCCCCGTCGG CTGGGTCGAG     60

GACCTCACCA AGGCGCAGGT CTCCTTCGCC CGGGAGCTGA CCGCCACGGT CACCACCACC    120

GCCCGCGATC TCCTCAAGTG A                                              141

(2) INFORMATION FOR SEQ ID NO: 13:

(i) SEQUENCE CHARACTERISTICS:
        (A) LENGTH: 10 base pairs
        (B) TYPE: nucleic acid
        (C) STRANDEDNESS: double
        (D) TOPOLOGY: unknown (xi) SEQUENCE DESCRIPTION: SEQ ID NO: 13:

GACTGGGCCC                                                            10

(2) INFORMATION FOR SEQ ID NO: 14:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (xi) SEQUENCE DESCRIPTION: SEQ ID NO: 14:

Met Thr Thr Ala Lys
1               5

(2) INFORMATION FOR SEQ ID NO: 15:

(i) SEQUENCE CHARACTERISTICS:
        (A) LENGTH: 46 amino acids
        (B) TYPE: amino acid
        (C) STRANDEDNESS: unknown
        (D) TOPOLOGY: unknown (xi) SEQUENCE DESCRIPTION: SEQ ID NO: 15:

Ser Ser Leu Leu Asp Leu Gln Glu Lys Leu Ala Ser Ala Ser Pro Val
1               5                   10                  15

Gly Trp Val Glu Asp Leu Thr Lys Ala Gln Val Ser Phe Ala Arg Glu
            20                  25                  30

Leu Thr Ala Thr Val Thr Thr Thr Ala Arg Asp Leu Leu Lys
        35                  40                  45

(2) INFORMATION FOR SEQ ID NO: 16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 16:

CCGCTCGAGG ATGCTCCGGG TACG                                            24

(2) INFORMATION FOR SEQ ID NO: 17:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 17:

TTTGGGCCCT CACTTCTCCT GCAGGTCGAG CAGGCTC                37

(2) INFORMATION FOR SEQ ID NO: 18:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 18:

TTTGGGCCCT CACTCCCGGG CGAAGGAGAC CTGCG                  35

(2) INFORMATION FOR SEQ ID NO: 19:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 19:

TTTGGGCCCT CAGACCCAGC CGACGGGGCT GGCGG                  35

(2) INFORMATION FOR SEQ ID NO: 20:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 20:

TTTGGGCCCT CACTTGGTGA GGTCCTCGAC CCAGC                  35

(2) INFORMATION FOR SEQ ID NO: 21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 21:

TTTGGATCCC TCGCCTCCGC CAGCCCCGTC                        30

(2) INFORMATION FOR SEQ ID NO: 22:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 22:

TTTGGATCCG ATATCTCACT TGAGGAGATC GCGGGCGG               38

(2) INFORMATION FOR SEQ ID NO: 23:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 23:

-continued

```
AAGAGATCTT CGGGCCCGTG GTA                                    23

(2) INFORMATION FOR SEQ ID NO: 24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 24:

TTTGGATCCG AAGAACCCGA GCGCGTTGGG                              30

(2) INFORMATION FOR SEQ ID NO: 25:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (xi) SEQUENCE DESCRIPTION: SEQ ID NO: 25:

Xaa Xaa Ala Lys Xaa Pro Val Asp Ala Ala Val Ala Lys
    1               5                   10

(2) INFORMATION FOR SEQ ID NO: 26:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (xi) SEQUENCE DESCRIPTION: SEQ ID NO: 26:

Glu Asp Leu Thr Lys
    1               5

(2) INFORMATION FOR SEQ ID NO: 27:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (xi) SEQUENCE DESCRIPTION: SEQ ID NO: 27:

Arg Asp Leu Leu Lys
    1               5
```

We claim:

1. An isolated gene encoding the polyhydroxyalkanoate (PHA) polymer granule-associated protein designated GA14, isolated from *Rhodococcus ruber*.

2. An isolated DNA molecule encoding a polyhydroxyalkanoate polymer granule-associated protein comprising a 1.0 kb XhoI-ApaI genomic restriction fragment from *Rhodococcus ruber*, said restriction fragment comprising SEQ ID NO:2.

3. A method of controlling polymer granule size and number in a bacterium that produces PHA, comprising inserting into the genome of said bacterium a gene encoding the *Rhodococcus ruber* polyhydroxyalkanoate polymer granule-associated protein GA14.

4. A method of binding a desired protein to a PHA granule in a bacterium which produces said granule, comprising inserting into the genome of said bacterium a DNA which encodes said desired protein and also encodes the HD1 and/or HD2 domain of the *Rhodococcus ruber* GA14 protein.

5. A bacterium transformed with genes encoding enzymes necessary for catalyzing the production of polyhydroxyalkanoate operably linked to gene regulatory sequences for controlling expression of said genes, and further transformed with a gene encoding a *Rhodococcus ruber* GA14 polyhydroxyalkanoate polymer granule-associated protein or a fusion gene encoding a *Rhodococcus ruber* GA14 polyhydroxyalkanoate polymer granule-associated fusion protein.

* * * * *